US012802788B2

(12) United States Patent
Minzner

(10) Patent No.: US 12,802,788 B2
(45) Date of Patent: Nov. 17, 2026

(54) MACHINE-LEARNING TECHNIQUES FOR GENERATING ADVERSE-EVENT REPORTS

(71) Applicant: TrialSpark, Inc., New York, NY (US)

(72) Inventor: Josh Minzner, Astoria, NY (US)

(73) Assignee: FORMATION BIO, INC., New York, NY (US)

( * ) Notice: Subject to any disclaimer, the term of this patent is extended or adjusted under 35 U.S.C. 154(b) by 0 days.

(21) Appl. No.: 19/288,630

(22) Filed: Aug. 1, 2025

(65) Prior Publication Data

US 2026/0038649 A1 Feb. 5, 2026

Related U.S. Application Data

(60) Provisional application No. 63/678,942, filed on Aug. 2, 2024.

(51) Int. Cl.
*G16H 10/20* (2018.01)
*G16H 15/00* (2018.01)

(52) U.S. Cl.
CPC ............. *G16H 10/20* (2018.01); *G16H 15/00* (2018.01)

(58) Field of Classification Search
CPC ........ G16H 10/20; G16H 10/60; G16H 50/70; G16H 20/10; G16H 70/40; G16H 10/00
See application file for complete search history.

(56) References Cited

U.S. PATENT DOCUMENTS

2020/0335188 A1* 10/2020 Ozeran ................. G06F 40/174
2022/0172805 A1 6/2022 Liu et al.
2022/0319652 A1 10/2022 Ozeran

FOREIGN PATENT DOCUMENTS

WO 2021/211881 A1 10/2021

OTHER PUBLICATIONS

"One at a Time; Producing Patient Profiles and Narratives", JJ Hantsch, et al. SAS Global Forum 2012, Paper 211-2012 (Year: 2012).*
International Search report and Written Opinion of International Patent Application No. PCT/US2025/040344, Oct. 9, 2025, 15 pages.

* cited by examiner

*Primary Examiner* — Joseph D Burgess
(74) *Attorney, Agent, or Firm* — POLSINELLI PC

(57) ABSTRACT

Disclosed embodiments may provide techniques for generating adverse-event reports using machine-learning models. A computer-implemented method can include receiving a selection of a particular subject from a plurality of subjects participating on a clinical trial. A plurality of identifiers associated with the plurality of subjects can be displayed on a first portion of a user interface. The computer-implemented method can also include accessing clinical data associated with a particular subject, in which the clinical data includes a plurality of clinical-data items. The computer-implemented method can also include receiving a request to generate an adverse-event report. The computer-implemented method can also include processing the clinical data using a machine-learning model to generate one or more sections associated with the adverse-event report. The computer-implemented method can also include causing the one or more sections associated with the adverse-event report to be displayed on a second portion of the user interface.

24 Claims, 6 Drawing Sheets

MACHINE-LEARNING TECHNIQUES FOR GENERATING ADVERSE-EVENT REPORTS

CROSS-REFERENCES TO RELATED APPLICATIONS

The present patent application claims the benefit of priority to U.S. Provisional Patent Application 63/678,942 filed Aug. 2, 2024, which is incorporated herein by reference in its entirety for all purposes.

FIELD

The present disclosure relates generally to generating adverse-event reports. In one example, the systems and methods described herein may be used to generate adverse-event reports using machine-learning techniques.

SUMMARY

Disclosed embodiments may provide techniques for generating adverse-event reports using machine-learning models. A computer-implemented method can include receiving a selection of a particular subject from a plurality of subjects participating on a clinical trial. A plurality of identifiers associated with the plurality of subjects can be displayed on a first portion of a user interface associated with a document-processing application, at which an identifier corresponding to the particular subject can be selected. The computer-implemented method can also include accessing clinical data associated with a particular subject, in which the clinical data includes a plurality of clinical-data items. In some instances, each of the plurality of clinical-data items is accessed from one or more clinical-data sources. The one or more clinical-data sources can include various types of data sources. For example, the one or more clinical-data sources can include an adverse-event data source that identifies the one or more adverse events. The one or more clinical-data items associated with the adverse-event data source can identify demographic data associated with the particular subject. In another example, the one or more clinical-data sources can include concomitant-medications data source that identifies one or more types of medications consumed by the particular subject before or during the clinical trial. In yet another example, the one or more clinical-data sources can include a laboratory-results data source that identifies various clinical results that were measured for the particular subject during the clinical trial.

The computer-implemented method can also include causing the plurality of clinical-data items to be displayed on the first portion of the user interface. The computer-implemented method can also include receiving a request to generate an adverse-event report. For example, the request can be initiated by interacting with one or more user-interface elements of the extension application associated with the report-generating application. In some instances, the adverse-event report can include a chronological description of one or more adverse events associated with the particular subject, in which the one or more adverse events were identified during participation of the particular subject for the clinical trial.

The computer-implemented method can also include processing the clinical data using a machine-learning model to generate one or more sections associated with the adverse-event report. The machine-learning model can be trained using a training dataset that includes previous adverse-event reports associated with other clinical trials. In some instances, the one or more sections of the adverse-event report can include an electronic link, in which the electronic link identifies a corresponding clinical-data item from the first portion of the user interface.

The computer-implemented method can also include causing the one or more sections associated with the adverse-event report to be displayed on a second portion of the user interface of the document-processing application. In some instances, the report-generating application receives modifications to the one or more sections of the adverse-event report. The report-generating application can generate feedback data based on the modifications, in which the feedback data can be used to further train the machine-learning model.

In an embodiment, a system comprises one or more processors and memory including instructions that, as a result of being executed by the one or more processors, cause the system to perform the processes described herein. In another embodiment, a non-transitory computer-readable storage medium stores thereon executable instructions that, as a result of being executed by one or more processors of a computer system, cause the computer system to perform the processes described herein.

Various embodiments of the disclosure are discussed in detail below. While specific implementations are discussed, it should be understood that this is done for illustration purposes only. A person skilled in the relevant art will recognize that other components and configurations can be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which can be exhibited by some embodiments and not by others.

The terms used in this specification generally have their ordinary meanings in the art, within the context of the disclosure, and in the specific context where each term is used. Alternative language and synonyms can be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles can be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

BRIEF DESCRIPTION OF THE DRAWINGS

Illustrative embodiments are described in detail below with reference to the following figures.

Figure 1:
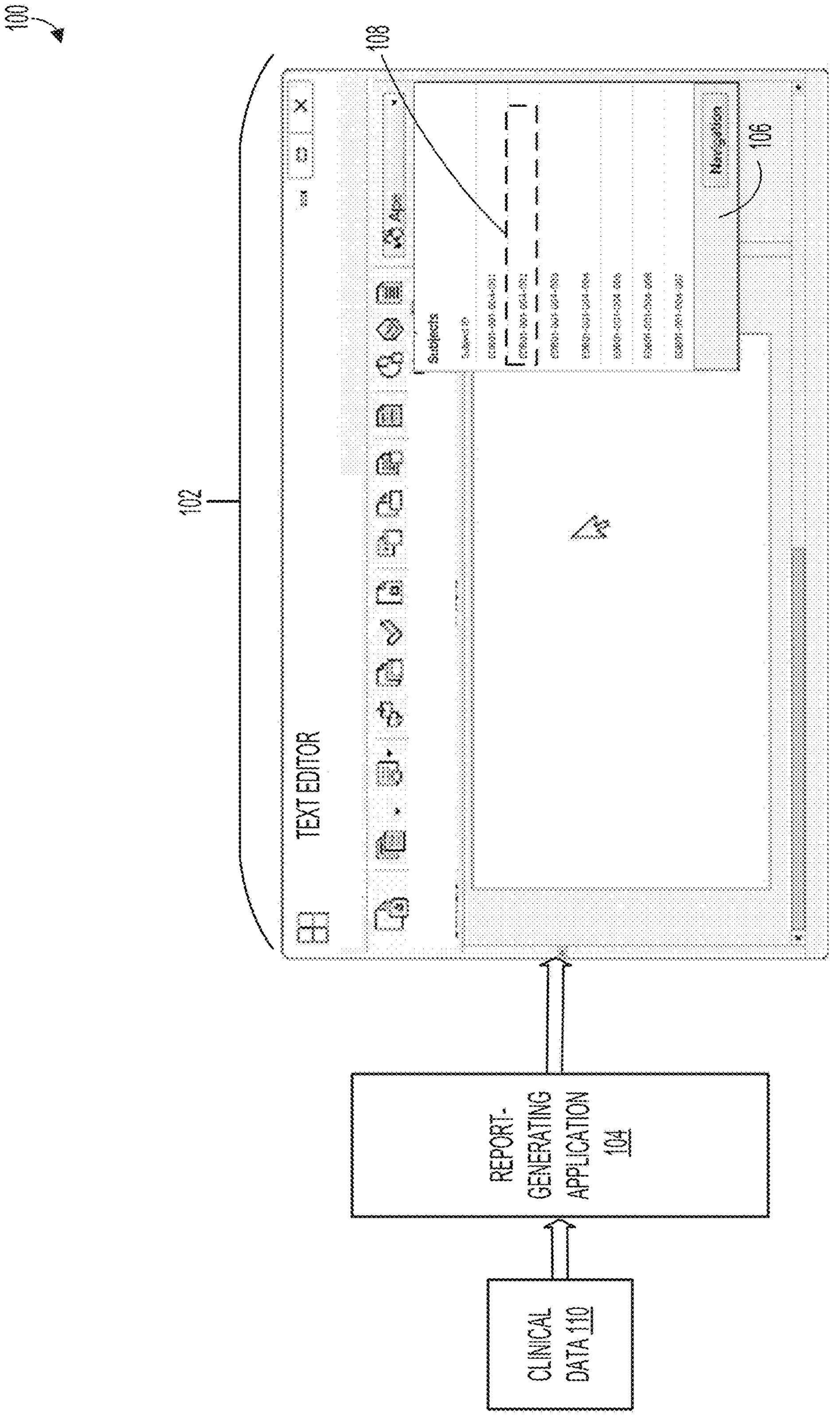
FIG. 1 illustrates an example schematic diagram for accessing clinical data for generating adverse-event reports, according to some embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

In the following description, for the purposes of explanation, specific details are set forth in order to provide a thorough understanding of certain inventive embodiments. However, it will be apparent that various embodiments may be practiced without these specific details. The figures and description are not intended to be restrictive. The word "exemplary" is used herein to mean "serving as an example, instance, or illustration." Any embodiment or design described herein as "exemplary" is not necessarily to be construed as preferred or advantageous over other embodiments or designs.

Subjects participating in clinical trials are subject to a possibility of experiencing adverse events, which can range from minor medical side effects such as headaches and nausea to more severe conditions like heart attacks. These adverse events may occur irrespective of their connection to the drug being tested. The Food and Drug Administration (FDA) requires pharmaceutical companies to meticulously compile and report these adverse events in a standardized format as part of the drug approval process. This requirement ensures that any potential risks associated with a new drug are thoroughly documented and evaluated.

The process of collecting and documenting these adverse events can be intricate and labor-intensive. Each adverse event must be carefully recorded and transformed into a clinical narrative report. This narrative is then be reviewed by medical experts to ensure its accuracy and completeness. On average, the report-preparation process can take approximately ten hours per adverse event. The time and expertise required make this task time-consuming and cumbersome. When outsourced to third-party service providers or specialized tools, the expenses can quickly escalate, often requiring a large amount of resources per clinical trial. These challenges underscore the need for an efficient solution to streamline the documentation and reporting of adverse events in clinical trials.

To address these challenges, disclosed embodiments may thus provide techniques for generating adverse-event reports by processing the clinical data using a machine-learning model. A report-generating application can receive a selection of a particular subject from a plurality of subjects participating on a clinical trial. A plurality of identifiers associated with the plurality of subjects can be displayed on a first portion of a user interface associated with a document-processing application, at which an identifier corresponding to the particular subject can be selected. As an illustrative example, the report-generating application is presented at a task pane of a document-processing application. The task pane displays the identifiers of different subjects participating in a clinical trial for immune checkpoint inhibitors (ICIs) associated with Hepatocellular carcinoma. A user interacts with the task pane to click on a link corresponding to an identifier associated with the particular subject of the clinical trial, at which the report-generating application can receive the selection and retrieve the relevant clinical data.

The report-generating application can access clinical data associated with a particular subject, in which the clinical data includes a plurality of clinical-data items. In some instances, each of the plurality of clinical-data items is accessed from one or more clinical-data sources. The one or more clinical-data sources can include various types of data sources. For example, the one or more clinical-data sources can include an adverse-event data source, concomitant-medications data source, and a laboratory-results data source. Continuing with the example, the report-generating application receives the selection of the particular subject, constructs an API request or database query for accessing the clinical data of the particular subject, and transmits the API request or database query to one or more storage servers to retrieve the clinical data from clinical-data sources.

The report-generating application causes the plurality of clinical-data items to be displayed on the first portion of the user interface. For example, the plurality of clinical-data items can be displayed on a task pane, a toolbar, and/or a dialog box associated with the document-processing application. The report-generating application can receive a request to generate an adverse-event report. For example, the request can be initiated by interacting with one or more user-interface elements associated with the report-generating application. Continuing with the example, the task pane of the document-processing application displays the clinical data associated with the subject. The user can then click on the "Generate Narrative" button to initiate a request to generate the adverse-event report.

The report-generating application can then process the clinical data using a machine-learning model to generate one or more sections associated with the adverse-event report. The machine-learning model can be trained using a training dataset that includes previous adverse-event reports associated with other clinical trials. In some instances, the one or more sections of the adverse-event report can include an electronic link, in which the electronic link identifies a corresponding clinical-data item from the first portion of the user interface. In some instances, the one or more sections of the adverse-event report includes one or more empty data fields.

The report-generating application can cause the one or more sections associated with the adverse-event report to be displayed on a second portion of the user interface of the document-processing application. Continuing with the example, the report-generating application displays the one or more sections of the adverse-event report on the task pane of the document-processing application. Clinical data indicated in the adverse-event report are formatted as hyperlinks that can point to the corresponding clinical-data items shown on the task pane of the report-generating application. The one or more sections of the adverse-event report also includes empty data fields that can be filled out by the user. In some instances, the report-generating application receives modifications to the one or more sections of the adverse-event report. The report-generating application can generate feedback data based on the modifications, in which the feedback data can be used to further train the machine-learning model (e.g., reinforcement learning).

I. Techniques for Generating Adverse-Event Reports Using Machine-Learning Models

A. Example Implementation

As described herein, a report-generating application can be implemented to generate adverse-event reports by processing the clinical data using a machine-learning model. FIG. 1 illustrates an example schematic diagram 100 for accessing clinical data for generating adverse-event reports, according to some embodiments. In FIG. 1, a document-processing application 102 can launch an application extension that corresponds to the report-generating application 104. In some instances, the report-generating application 104 includes a user interface 106 that is configured to receive a selection 108 of a particular subject associated with the clinical trial. The user interface 106 can correspond to a portion of a larger user interface displayed by the document-processing application 102. To preserve privacy of the subjects, an identifier representing the particular subject can be displayed on the user interface 106, in which the identifier can be generated to prevent exposure of the subject's personal identifiable information (PII). For example, the identifier of the particular subject associated with the selection 108 can correspond to "EDB01-001-004-002". Once the subject is selected, the report-generating application 104 can access clinical data 110 associated with the particular subject.

Figure 2:
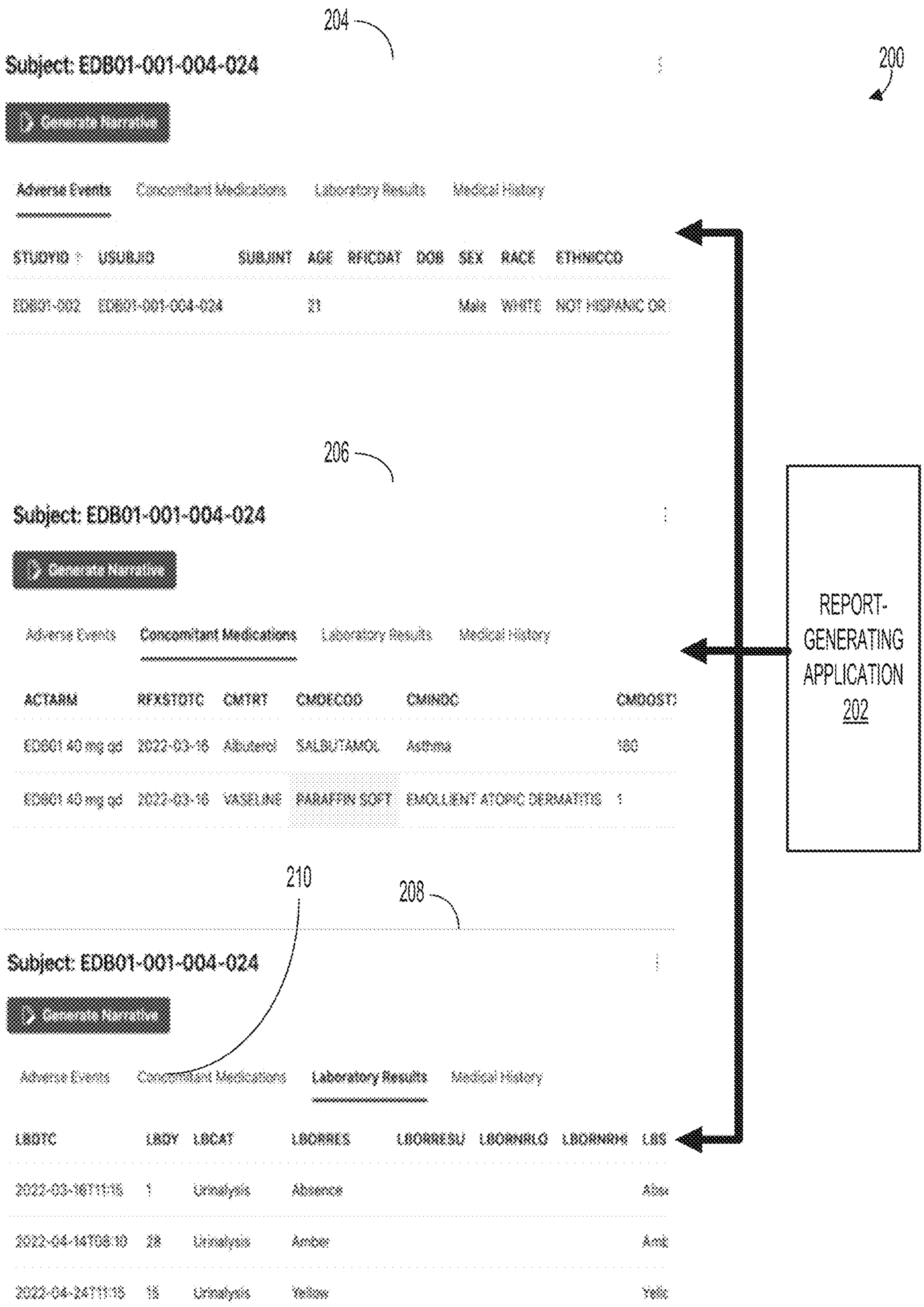
FIG. 2 illustrates example screenshots of clinical data accessed from clinical-data sources, according to some embodiments.

In some instances, the clinical data 110 can be accessed from various data sources. FIG. 2 illustrates example screenshots 200 of clinical data accessed from one or more clinical-data sources, according to some embodiments. In FIG. 2, a report-generating application 202 (e.g., the report-generating application 104 of FIG. 1) displays one or more types of clinical-data sources 204, 206, and 208 for the subject as identified by an identifier. A first example type of clinical-data source includes an adverse-event data source 204 that identifies specific adverse events associated with the subject, including a description of the severity, duration, and any mitigating factors associated with the adverse events. In some instances, the adverse-event data source 204 identifies: (i) a clinical-trial identifier that identifies a clinical trial for which the adverse event was detected; and (ii) demographic data that identifies various demographic information associated with the subject. In some instances, the demographic data associated with the subject includes, but are not limited to, age, gender, ethnicity, geographic location, socioeconomic status, language, and household size.

A second example type of clinical-data source includes a concomitant-medications data source 206 that identifies various types of medications consumed by the subject before or during the clinical trial. The concomitant-medications data source 206 can be used to identify potential drug interactions between the primary drug and the concomitant drug(s) and any side effects associated with the concomitant drug(s). As shown in FIG. 2, the concomitant-medications data source 206 shows an Actual Treatment Arm (ACTARM) data field that identifies specific treatment group or arm to which the subject was assigned and actually received during the clinical trial. The ACTARM can include various study arms such as placebo, experimental treatment, standard of care, etc. The concomitant-medications data source 206 can also include a Concomitant Medication Treatment (CMTRT) data field that identifies concomitant medications taken by the subject alongside the primary treatment being studied during the clinical trial. The concomitant-medications data source 206 can also include a Concomitant Medication Dictionary-Derived Name (CMDECOD) data field that represents the standardized term or description of a concomitant medication, in which the standardized term is derived from a controlled vocabulary or dictionary (e.g., WHO Drug Dictionary). The CMDECOD can ensure uniformity and consistency in the reporting and analysis of concomitant medications across the study.

A third example type of clinical-data source includes a laboratory-results data source 208, which identifies various clinical results that were measured for the subject during the clinical trial. The laboratory-results data source 208 can be used to integrate empirical data supporting the adverse-event report and identify a scientific basis for the observations made during the clinical trial. For example, the laboratory-results data source 208 can include a study day (LBDY) data field that represents the specific day relative to the start of the clinical trial on which a laboratory test was performed. The LBDY information can be used to track the timing of laboratory assessments in relation to the overall study timeline. Another example of the laboratory-results data source 208 can include a laboratory category (LBCAT) data field that identifies a type of laboratory test performed, such as hematology, biochemistry, and urinalysis. A third example of the laboratory-results data source 208 can include a Laboratory Test Result Original (LBORRES) data field that identifies the original result or value obtained from a laboratory test before any conversions or standardizations are applied. The LBORRES can identify the raw data collected from the laboratory analysis. Other fields for the laboratory-results data source can include a Laboratory Test Result Lower Limit of Normal (LBORNRLO) data field and a Laboratory Test Result Upper Limit of Normal (LBORNRHI) data field that identifies respective lower and upper reference limits that can be used to assess whether the subject's laboratory results fall within normal or expected values. Other example types of clinical-data sources can include a medical-history data source (not shown) that identifies medical history associated with subject, including preexisting health conditions and consumed medications.

The report-generating application 202 can receive a request to generate an adverse-event report based on the clinical data associated with the particular subject. As shown in FIG. 2, the request is initiated by interacting with one or more user-interface elements of the extension application, such as clicking on a "Generate Narrative" element 210. Other examples of user-interactions can be implemented to initiate the request, including but not limited to typing the request, swiping, tapping the user-interface element, hovering over the user-interface element, and double-clicking the user-interface element.

Figure 3:
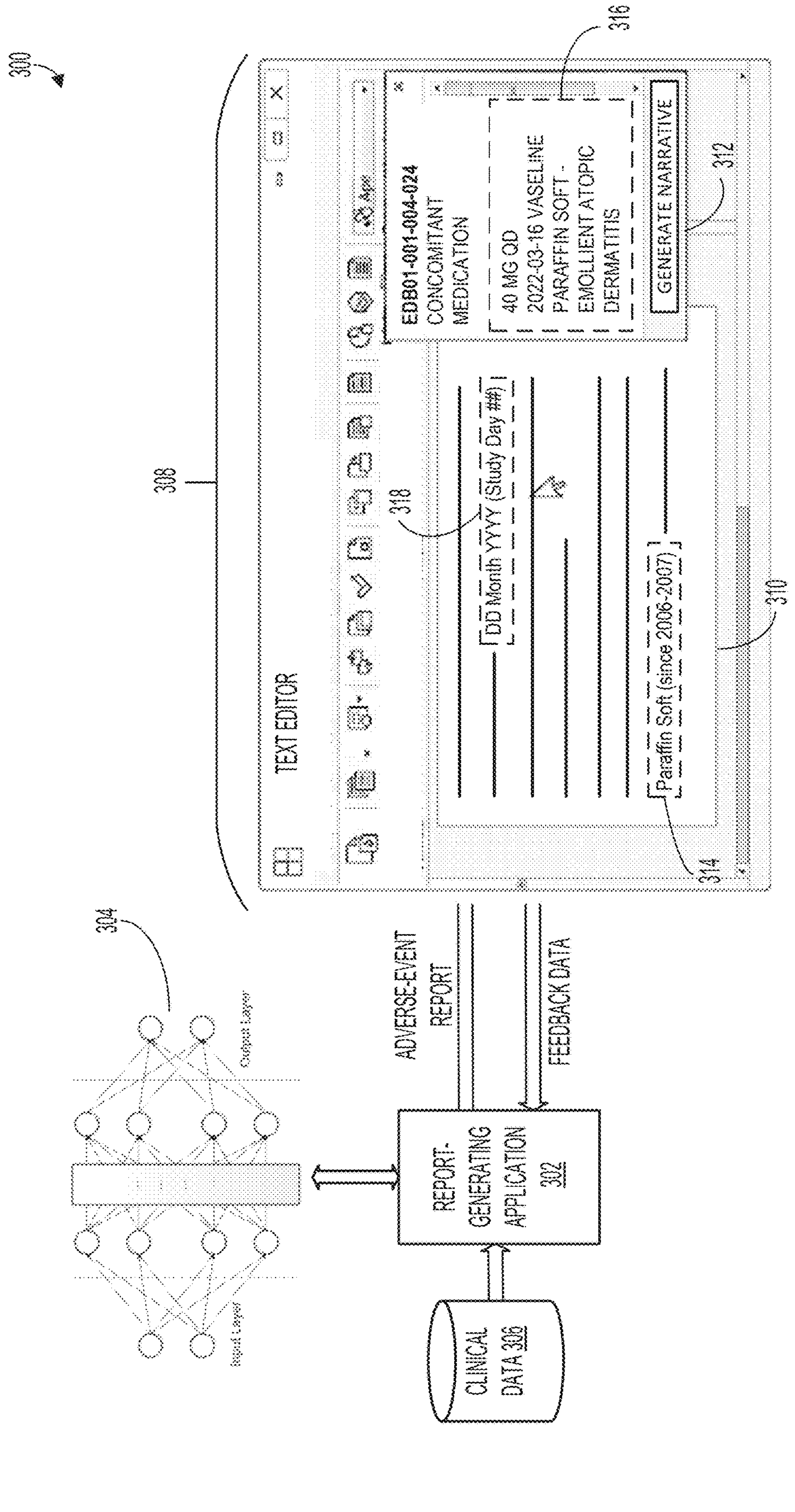
FIG. 3 illustrates an example schematic diagram for generating adverse-event reports clinical data accessed from clinical-data sources, according to some embodiments.

FIG. 3 illustrates an example schematic diagram 300 for generating adverse-event reports based on clinical data accessed from clinical-data sources, according to some embodiments. As shown in FIG. 3, a report-generating application 302 (e.g., the report-generating application 104 of FIG. 1) can use a machine-learning model 304 to process clinical data 306 (e.g., the clinical data 110 of FIG. 1), in which the machine-learning model 304 generates one or more sections of the adverse-event report. As used herein, the term "adverse-event report" or "adverse-event narrative" refers to a comprehensive description of one or more adverse medical events, in which the report can be included in clinical study reports, regulatory submissions, and pharmacovigilance documents. In some instances, the adverse-event report provides a chronological description of the adverse event, integrating clinical judgment and interpretation to offer a clear understanding of the event's context and implications. In some instances, the one or more text sections of the adverse-event report incorporate clinical-data objects associated with one or more types of clinical-data sources (e.g., the adverse-event data source, the concomitant-medications data source, the laboratory-results data source, the medical-history data source). Each section of the one or more sections can include text data, image data, audio data, video data, and/or any links thereto (e.g., a hyperlink of a video file).

In some instances, the machine-learning model 304 can output one of various sections associated with the adverse-event report. An example section can include an introduction section that provides a background section that describes the subject's condition, the treatment being studied, and the context in which the adverse event occurred. A second example section can include clinical-measurement section of the adverse event, including timing (onset, duration), symptoms, and any relevant laboratory or diagnostic findings. A third example section can include a clinical-context section that provides the subject's medical history, concomitant medications, and other factors that might have influenced the occurrence of the adverse event. The clinical-context section can also include any modifications to the treatment, such as dose adjustments, discontinuation, or additional therapies provided in response to the adverse event. Other examples of the sections can include: (i) a narrative section that describes a resolution of the adverse event, including whether the patient recovered, experienced ongoing issues, or had a fatal outcome; (ii) an evaluation section that describes the relationship between the treatment and the adverse event, supported by clinical reasoning and relevant evidence; and (iii) a conclusion section that summarizes the adverse event's significance in the context of the clinical trial or medical treatment, and any recommendations for future monitoring or investigation.

Examples of the machine-learning model 304 can include algorithms such as k-means clustering algorithms, fuzzy c-means (FCM) algorithms, expectation-maximization (EM) algorithms, hierarchical clustering algorithms, and density-based spatial clustering of applications with noise (DBSCAN) algorithms, in which the algorithms can be trained using unsupervised learning. Other examples of the machine-learning model 304 can include, but are not limited to, genetic algorithms, backpropagation, reinforcement learning, decision trees, linear classification, artificial neural networks, anomaly detection, and such. In yet other examples, the machine-learning model 304 may include regression analysis, dimensionality reduction, metalearning, reinforcement learning, deep learning, and other such algorithms and/or methods.

In some instances, the machine-learning model 304 is a transformer model (e.g., a large-language model (LLM)) obtained from a models database. In some instances, the machine-learning model 304 is trained using self-supervised learning based on a large corpus of text data, such that the machine-learning model 304 can generate the adverse-event report. In addition to training the model, various prompts can be used for prompt engineering of the machine-learning model 304 for generating the adverse-event report. Examples of the machine-learning model 304 can include, but are not limited to, BERT model, Claude LLM, Falcon 40B, Ernic, GPT-3, GPT-3.5, GPT 4, Lamda, and Llama.

Additionally or alternatively, the one or more sections of the adverse-event report can be generated according to regulatory data associated with one or more regulatory agencies. Such modification to the one or more sections can facilitate regulatory review and approval. In some instances, the one or more sections of the adverse-event report are further processed for formatting, compliance checks, and automated validation to ensure adherence to regulatory standards. The additional processing can not only ensure compliance with regulatory standards but also enhance the overall reliability and credibility of the clinical-trial results.

The report-generating application 302 can transmit the one or more sections of the adverse-event report, such that the one or more sections can be presented on a user interface. A document-processing application 308 (e.g., the document-processing application 102 of FIG. 1) can receive and display the one or more sections of the adverse-event report on its user interface. In some instances, the user can modify (e.g., add, replace, delete) at least part of the one or more sections of the adverse-event report by interacting with the user interface associated with the document-processing application 308. In FIG. 3, a left portion of the document-processing application 308 shows a first user interface 310 that displays the one or more sections of the adverse-event report. A right portion of the document-processing application 308 shows a second user interface 312 that displays the clinical data 306 accessed by the report-generating application 302.

The one or more sections of the adverse-event report can be configured to distinguish the clinical-data objects accessed from clinical-data sources (e.g., the adverse-event data source, the concomitant-medications data source, the laboratory-results data source) from other parts of the adverse-event report. For example, each clinical-data object displayed on the first user interface 310 can be presented as a link (e.g., a hyperlink, a reference link, a bookmark) that directs to a corresponding location of the clinical data displayed on the second user interface 312. Continuing with the example in FIG. 3, a text element 314 that refers to administering paraffin can be formatted as the link that refers to the corresponding data object 316 in the concomitant-medications data source. In some instances, the one or more sections of the adverse-event report can be configured to indicate empty data fields that can be inputted by the user. For example, a text element 318 indicates the user to input a date at which the drug has be administered. These configurations can be displayed on the first user interface 310 to facilitate any modifications of content associated with the one or more sections of the adverse-event report.

In some instances, the report-generating application 302 can include an audit component. The audit component can be configured to log every action taken within the one or more sections of the adverse-event report, including a description of data entries, modifications to the sections, and other operations associated with generating adverse-event report. The audit component can ensure transparency and accountability of the report-generating process, as well as for facilitating preparation for any future regulatory audits.

In some instances, any modifications to the one or more sections of the adverse-event report are used as feedback data. The feedback data can be used to further train the machine-learning model 304 (e.g., by adjusting one or more of its parameters), such that the machine-learning model 304 can be optimized to generate adverse-event reports that comply with regulatory requirements.

B. Computing Environment

Figure 4:
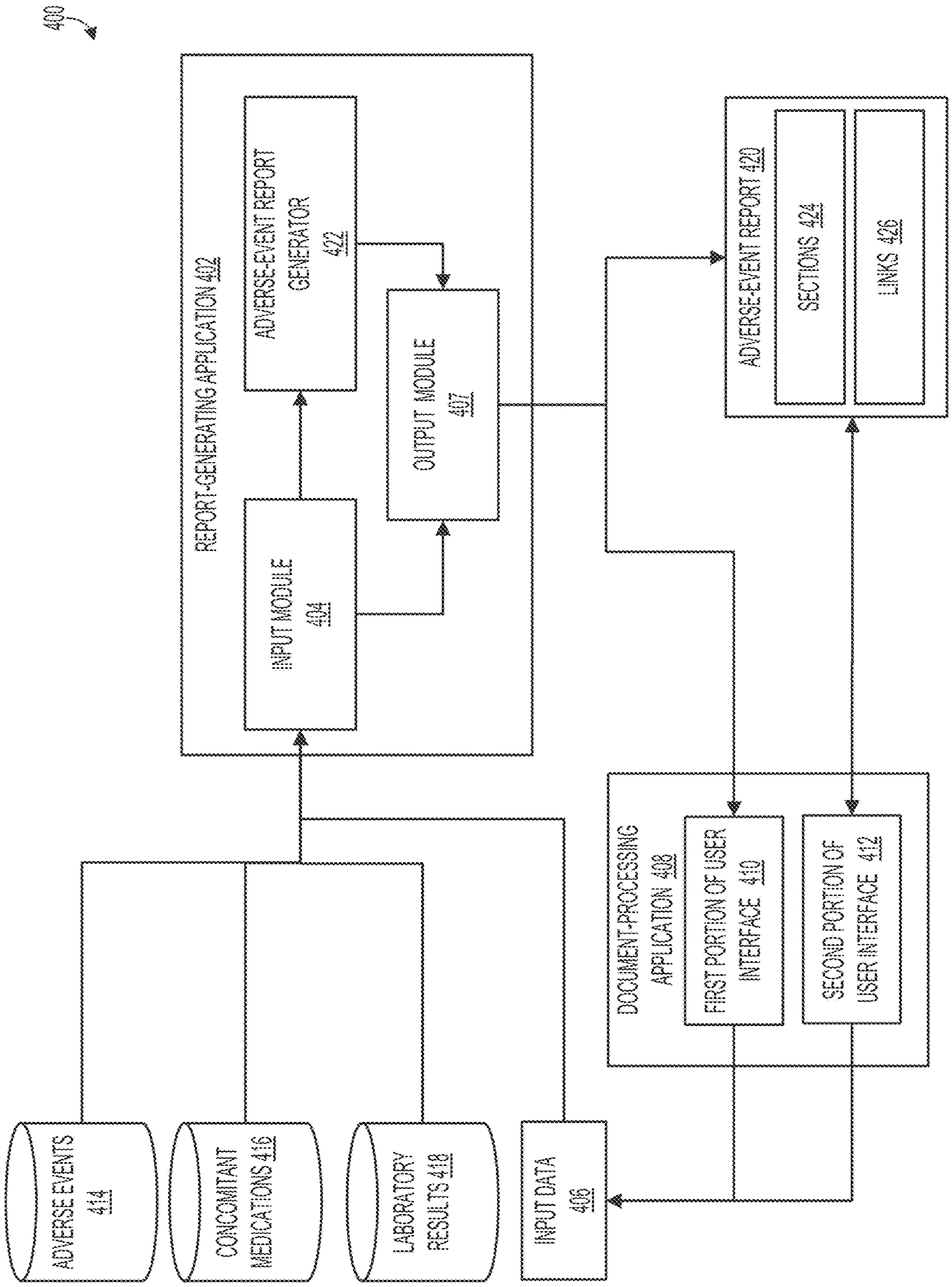
FIG. 4 illustrates an example computing environment for generating adverse-event reports based on clinical data accessed from clinical-data sources, according to some embodiments.

FIG. 4 illustrates an example computing environment 400 for generating adverse-event reports based on clinical data accessed from clinical-data sources, according to some embodiments. In FIG. 4, an input module 404 of a report-generating application 402 receives input data 406, which can include a selection of a particular subject from a plurality of subjects participating on a clinical trial. The particular subject can be selected by a user interacting with one or more graphical user-interface elements presented on a portion of a document-processing application. A document-processing application is a type of software application designed to create, edit, format, and print text-based documents. The document-processing application can include the following example features: (i) inputting and editing text; (ii) formatting documents; (iii) spelling and grammar check; (iv) exporting into different file formats; and (v) printing the documents.

The document-processing application can be associated with a user device. The user device can be a client device that includes a desktop computer system, a laptop or notebook computer system, a tablet computer system, a wearable computer system or interface, an interactive kiosk, a mainframe, a mesh of computer systems, a mobile telephone, a personal digital assistant (PDA), or a combination of two or more of these.

The input data 406 can be transmitted across a communication network. The network can be any network including an internet, an intranet, an extranet, a cellular network, a Wi-Fi network, a local area network (LAN), a wide area network (WAN), a satellite network, a Bluetooth® network, a virtual private network (VPN), a public switched telephone network, an infrared (IR) network, an internet of things (IoT network) or any other such network or combination of networks. Communications by the client device via the network can be wired connections, wireless connections, or combinations thereof. Communications via the network can be made via a variety of communications protocols including, but not limited to, Transmission Control Protocol/Internet Protocol (TCP/IP), User Datagram Protocol (UDP), protocols in various layers of the Open System Interconnection (OSI) model, File Transfer Protocol (FTP), Universal Plug and Play (UPnP), Network File System (NFS), Server Message Block (SMB), Common Internet File System (CIFS), and other such communications protocols.

An output module 407 of the report-generating application 402 can output a plurality of identifiers associated with the plurality of subjects, which can be displayed on a first portion 410 of a user interface associated with a document-processing application 408, at which an identifier corresponding to the particular subject can be selected. In some instances, a second portion 412 of the user interface is configured to display content (e.g., text data) inputted by the user. In some instances, the plurality of identifiers are generated to prevent exposure of the subject's personal identifiable information (PII). For example, the identifier of the particular subject can correspond to "EDB01-001-004-002", which obfuscates the PII of the particular subject.

1. Input Module

The input module 404 can receive clinical data associated with a particular subject, wherein the clinical data includes a plurality of clinical-data items. In some instances, each of the plurality of clinical-data items is accessed from clinical-data sources 414-418. A first example type of clinical-data source 414 includes an adverse-event data source that identifies specific adverse events associated with the subject, including a description of the severity, duration, and any mitigating factors associated with the adverse events. In some instances, the adverse-event data source 414 identifies: (i) a clinical-trial identifier that identifies a clinical trial for which the adverse event was detected; and (ii) demographic data that identifies various demographic information associated with the subject. In some instances, the demographic data associated with the subject includes, but are not limited to, age, gender, ethnicity, geographic location, socioeconomic status, language, and household size.

A second example type of clinical-data source includes a concomitant-medications data source 416 that identifies various types of medications consumed by the subject before or during the clinical trial. The concomitant-medications data source 416 can be used to identify potential drug interactions between the primary drug and the concomitant drug(s) and any side effects associated with the concomitant drug(s). The concomitant-medications data source 416 identifies an Actual Treatment Arm (ACTARM) data field that identifies specific treatment group or arm to which the subject was assigned and actually received during the clinical trial. The ACTARM can include various study arms such as placebo, experimental treatment, standard of care, etc. The concomitant-medications data source 416 can also include a Concomitant Medication Treatment (CMTRT) data field that identifies concomitant medications taken by the subject alongside the primary treatment being studied during the clinical trial. The concomitant-medications data source 416 can also include a Concomitant Medication Dictionary-Derived Name (CMDECOD) data field that represents the standardized term or description of a concomitant medication, in which the standardized term is derived from a controlled vocabulary or dictionary (e.g., WHO Drug Dictionary). The CMDECOD can ensure uniformity and consistency in the reporting and analysis of concomitant medications across the study.

A third example type of clinical-data source includes a laboratory-results data source 418, which identifies various clinical results that were measured for the subject during the clinical trial. The laboratory-results data source 418 can be used to integrate empirical data supporting the adverse-event report and identify a scientific basis for the observations made during the clinical trial. For example, the laboratory-results data source 418 can include a study day (LBDY) data field that represents the specific day relative to the start of the clinical trial on which a laboratory test was performed. The LBDY information can be used to track the timing of laboratory assessments in relation to the overall study timeline. Another example of the laboratory-results data source 418 can include a laboratory category (LBCAT) data field that identifies a type of laboratory test performed, such as hematology, biochemistry, and urinalysis. A third example of the laboratory-results data source can include a Laboratory Test Result Original (LBORRES) data field that identifies the original result or value obtained from a laboratory test before any conversions or standardizations are applied. The LBORRES can identify the raw data collected from the laboratory analysis. Other fields for the laboratory-results data source can include a Laboratory Test Result Lower Limit of Normal (LBORNRLO) data field and a Laboratory Test Result Upper Limit of Normal (LBORNRHI) data field that identifies respective lower and upper reference limits that can be used to assess whether the subject's laboratory results fall within normal or expected values. Other example types of clinical-data sources can include a medical-history data source (not shown) that identifies medical history associated with subject, including preexisting health conditions and consumed medications.

After receiving the clinical data from the clinical-data sources 414-418, the report-generating application 402 can then display the clinical data on the first portion 410 of the user interface. Stated differently, the output module 407 causes the plurality of clinical-data items to be displayed on the first portion 410 of the user interface. For example, the plurality of clinical-data items can be displayed on a task pane of a document-processing application 408. Task panes can include dockable windows that present the clinical-data items and interact with the user. The task panes can be placed on the right, left, top, or bottom of the Word document. In other examples, the plurality of clinical-data items can also be displayed on a toolbar of the document-processing application 408 and/or content add-ins that facilitate interaction with the clinical-data items and other content presented on the second portion 412 of the document-processing application 408. Additionally or alternatively, the first portion 410 can be dialog boxes that require user interaction with the clinical-data items before returning to the user interface.

The input module 404 can additionally receive a request to generate an adverse-event report 420. For example, the request can be initiated by interacting with one or more user-interface elements displayed on the first portion 410 of the user interface, at which the request can be transmitted to the input module 404. Other examples of user-interactions can be implemented to initiate the request, including but not limited to typing the request, swiping, tapping the user-interface element, hovering over the user-interface element, and double-clicking the user-interface element. As described herein, the adverse-event report 420 can include a comprehensive description of one or more adverse medical events, in which the report can be included in clinical study reports, regulatory submissions, and pharmacovigilance documents. In some instances, the adverse-event report 420 can include a chronological description of one or more adverse events associated with the particular subject, in which the one or more adverse events were identified during participation of the particular subject for the clinical trial.

2. Adverse-Event Report Generator

An adverse-event report generator 422 of the report-generating application 402 processes the clinical data using a machine-learning model to generate one or more sections 424 associated with the adverse-event report 420. The machine-learning model can be trained using a training dataset that includes previous adverse-event reports associated with other clinical trials. The following description can provide an example scheme of using the machine-learning model to generate the adverse-event report 420 based on the accessed clinical data-items associated with the particular subject.

a. Model Selection

In some instances, the machine-learning model can be generated based on different types of machine-learning architectures. An example architecture used for transformer models can include a transformer model that includes an encoder and a decoder. Another example can include a Bidirectional Encoder Representations from Transformers (BERT), which is configured to understand the context of a word in search queries by considering the words on both its left and right.

In yet another example, a machine-learning architecture can include a Generative Pre-trained Transformer (GPT) that is trained using autoregressive language modeling and masked self-attention techniques. For example, the masked self-attention techniques can include masking future tokens when generating a contextual representation representing a given token, such that the contextual representation is determined only based on past tokens. The autoregressive language modeling techniques can then predict the next token of an output sequence based on the contextual representations of the text tokens.

Other examples of machine-learning architectures can include: (1) a Text-to-Text Transfer Transformer (T5) that converts all natural-language processing tasks into a text-to-text format, unifying various tasks under a single model architecture; and (2) a Vision Transformer (ViT) that extends the transformer architecture to process longer text sequences and image data, respectively, thereby facilitating the corresponding model to be used across different domains.

b. Training Phase

For the training dataset (e.g., the previous input data and corresponding adverse-event report), the masked self-attention process can begin by transforming each word in a given training text sequence into three vectors: the query (Q), key (K), and value (V) vectors. A Q vector can represent what information the token is querying about other tokens, a K vector can represent the token's context used to establish relationships with other tokens, and a V vector can represent the token's actual content/information. In some instances, the Q, K, and V vectors can be obtained by multiplying the input embeddings by learned weight matrices.

An attention score for a particular word can be calculated by taking the dot product of the Q vector of the word with the K vectors of all words in the sequence, thereby producing a score that reflects the relevance of each word pair. The attention scores can be used as weights, which can be applied to the Q, K, V vectors to generate a weighted contextual representation of the particular word. Stated differently, the attention score can be used as a weight to transform the Q, K, V vectors of a given word to generate a weighted, computed representation that can be used to train the corresponding transformer model.

In some instances, a mask can be applied to the self-attention mechanism such that a contextual representation of a given token is determined without weights associated with future tokens. As a result, an attention score of a particular token can be adjusted to disregard information from tokens that have not been processed yet. The attention scores can then be scaled by the square root of the key dimension to stabilize training and passed through a softmax function to convert the attention scores into probabilities, ensuring they sum to one. The transformation can identify the most relevant words while downplaying less important ones. The resulting attention weights can then be used to compute a weighted sum of the V vectors, thus producing a new contextual representation for each token that incorporates contextual information from the entire sequence.

To enhance the model's ability to capture various types of relationships, self-attention mechanisms can use multiple sets of Q, K, and V matrices, also referred to as multi-head attention. Each set, or head, can learn different aspects of the relationships within the input data. The outputs from these heads can be concatenated and linearly transformed to form the final self-attention output. This multi-head approach allows the transformer models to simultaneously consider different features and interactions, enriching its understanding of the input sequence.

The transformer model can then be trained using autoregressive language modeling to predict a subsequent token of a target sequence based on the contextual representations that represent the preceding tokens. For each position in the sequence, the transformer model accesses a contextual representation of the token, which was generated using masked self-attention mechanism. The transformer model can then output a probability distribution over a vocabulary for the subsequent token, conditioned on the sequence of preceding tokens. The subsequent token can then be compared with a corresponding token of the training data to calculate a loss. The loss measures the discrepancy between the predicted token and the actual token, providing a signal for the model to adjust its parameters. The loss can then be used to adjust parameters of the transformer model, including the parameters of the Q, K, V matrices.

Through iterative training iterations, the transformer model learns to minimize this loss across the entire training dataset. This process ensures that the model generates coherent and contextually appropriate sequences by leveraging the learned representations and adjusting its parameters based on the training data.

c. Fine-Tuning Phase Using Prompts

In some instances, the adverse-event report generator 422 can construct one or more prompts that can be submitted with the clinical-data items to enhance and increase the accuracy of the adverse-event report 420. As used herein, the term "prompt" can refer to as an input sequence generated to direct a corresponding machine-learning model's generation process towards producing a target output. In some instances, a filtering prompt includes a sequence of text tokens in a specific format (e.g., text, XML data, JSON data) and language (e.g., English, Korean).

In some instances, the prompts are machine-generated prompts that are generated by one or more computer systems, in which the machine-generated prompts are generated without user intervention. For example, the one or more filtering prompts can be constructed using prompt engineering. Prompt engineering can include techniques for designing and implementing prompts within a machine-learning system to generate target responses or actions. In some instances, prompt engineering leverages a combination of linguistic approaches, machine-learning algorithms, and domain knowledge to formulate prompts that elicit specific outputs from a corresponding machine-learning model. The prompt engineering process typically begins with an analysis of a target or a problem domain, followed by the formulation of prompts tailored to achieve the desired results.

As an illustrative example for optimizing prompts, a prompt P can be defined as a sequence of tokens, tailored to elicit specific responses from a machine-learning model. The model employs an objective function O(P, R) to evaluate the quality of generated responses R given the prompt P. The responses R can be generated based on a machine-learning language model LM processing the prompt P (e.g., the function LM(P)). Different types of objective functions can be selected depending on the task and targeted output. For example, an objective function can correspond to a text summarization technique using ROUGE scores. In another example, the objective function can correspond to a translation quality assessment technique using BLEU scores. In some instances, optimization techniques like gradient descent or evolutionary algorithms are used iteratively refine the prompt P to maximize O(P,R), to facilitate the model to consistently produce accurate, relevant, and contextually appropriate outputs (e.g., the adverse-event report 420). For example, the optimal prompt P* can be determine based on maximizing the objective function O:

$$P^{*}=\text{argmax } O(P,\text{LM}(P)) \qquad \text{Equation (1)}$$

Through the iterative refinement process, prompt engineering enhances the corresponding model's performance across various natural language processing tasks, such as generating the adverse-event report 420 that is contextually relevant to the clinical-data items.

In some instances, prompt engineering includes a selection of input formats and structures. The input-format selection can include determining the syntactic and semantic characteristics of the prompts that will effectively guide the machine-learning model towards the desired outputs. In some instances, linguistics and computational linguistics can be used to select input formats that are semantically meaningful and contextually relevant. The input-format selection can ensure that the prompts effectively communicate the desired tasks or questions to the machine-learning model. The prompt engineering process can also include an optimization of prompt parameters. The optimization can include fine-tuning various parameters such as prompt length, complexity, and specificity to enhance the machine-learning model's performance on targeted tasks. Different prompt formulations and configurations such as grid search or Bayesian optimization can be implemented to optimize the prompt parameters. Additionally or alternatively, techniques such as zero-shot learning or few-shot learning can be implemented to fine-tune the machine-learning models to generalize from limited prompt examples.

The prompt engineering process can be configured based on an underlying machine-learning model architecture and training data. For example, an appropriate pre-trained machine-learning model architecture (e.g., GPT, BERT, or Transformer) that aligns with the task requirements and available computational resources can be identified for a given task. In some instances, the machine-learning model can be fine-tuned on task-specific data to further improve probability of outputting target responses. Various types of training datasets can be used to train and fine-tune the machine-learning model, so as to enable the machine-learning model to understand and generate responses to prompts accurately.

In some instances, an iterative process of designing, testing, and optimizing prompts is implemented based on feedback from initial model outputs. This iterative approach allows for continuous improvement and refinement of the prompt engineering process, ultimately leading to better-performing machine-learning models. Additionally or alternatively, ongoing monitoring and evaluation of model performance can be used to identify any errors or biases introduced by the prompts and prompt engineering process, in which the feedback data can be generated based on the evaluation. The feedback data can be used to further adjust the parameters of the machine-learning models, such that the machine-learning models can be updated to improve accuracy in generating the target responses.

d. Deployment Phase

The adverse-event report generator 422 can apply the trained and fine-tuned machine-learning model to the clinical-data items to generate the adverse-event report 420. To begin the deployment process, the adverse-event report generator 422 can tokenize the clinical-data items into a sequence of text tokensIn some instances, the machine-learning model uses Byte Pair Encoding (BPE) techniques to further split a single token (e.g., "in", "sufficient").

The adverse-event report generator 422 can assign each token with a particular index value in the vocabulary (e.g., "assistant"=E[5]). Then, the adverse-event report generator 422 can convert each token into a vector representation (e.g., an embedding) based on a pre-trained embedding matrix. For example, for a vocabulary size V and embedding dimension $d_i$, the embedding matrix E is of size V×d, in which the vector e; can be generated for the text token $t_i$ based on using the index value a looking of a corresponding row of embedding matrix E.

$$E{:}e_i=E[t_i] \quad \text{Equation(2)}$$

The adverse-event report generator 422 can then process the sequence of embeddings ($e_1$, $e_2$, $e_3$, . . . $e_n$) that represent the sequence of tokens by adding positional encodings to account for the order of tokens. In some instances, positional encodings are vectors added to each token embedding to inject information about the position of tokens in the sequence. A matrix X can be formed that includes the sequence of position-encoded vectors.

For the matrix X, the adverse-event report generator 422 can then determine a contextual representation for each position-encoded vector of the matrix X. In particular, for each position-encoded vector, the adverse-event report generator 422 can generate a set of Q, K, V vectors for the position-encoded vector. As described herein, a Q vector can represent what information the token is querying about other tokens, a K vector can represent the token's context used to establish relationships with other tokens, and a V vector can represent the token's actual content/information.

In some instances, to enhance the model's ability to capture various types of relationships, the position-encoded vector can be represented by multiple sets of Q, K, and V matrices (i.e., multi-head attention). Each set of Q, K, V vectors, or head, can learn different aspects of the relationships within the input data. The outputs from these heads can be concatenated and linearly transformed to form the final self-attention output. This multi-head approach allows the transformer models to simultaneously consider different features and interactions, enriching its understanding of the input sequence.

An attention score can be calculated for the set of Q, K, V vectors as follows:

$$\text{Attention}(Q,K,V)=\text{softmax}\left((QK^T)/\sqrt{(d_k)}\right)V \quad \text{Equation (3)}$$

The $(QK^T)/\sqrt{(d_k)}$ can be used to compute the raw attention scores, in which $d_k$ is the dimensionality of the key vectors. Then, the softmax function is applied to the raw attention score to normalize it into a probability distribution. The adverse-event report generator 422 can apply the attention score to a V vector of the corresponding set of Q, K, V vectors, such that the weighted Q, K, V vectors can be used as the contextual representation of the position-encoded vector of matrix X. In the instances in which multi-head attention is used, the multiple sets of weighted Q, K, V vectors can be concatenated and linearly transformed using a weight matrix $W^O$ to generate the contextual representation of the position-encoded vector. The above process can be iterated through other position-encoded vectors of matrix X to generate a set of contextual representations associated with the merged data.

The adverse-event report generator 422 can then apply the machine-learning model to the set of contextual representations to generate the adverse-event report 420. In particular, the machine-learning model can process the set of contextual representations to predict each token of the output, in which the outputted tokens can correspond to the one or more sections 424 of the adverse-event report 420.

e. Output Characteristics

In some instances, the one or more sections 424 of the adverse-event report 420 can include electronic links 426, in which an electronic link identifies a corresponding clinical-data item from the first portion 410 of the user interface. In some instances, the one or more sections 424 of the adverse-event report 420 includes one or more empty data fields. For example, a text element can displayed on the second portion 412 of the user interface to receive a date at which the drug has be administered. These configurations can be displayed on the second portion 412 to facilitate any modifications of content associated with the one or more sections of the adverse-event report 420.

In some instances, the machine-learning model can output one of various sections 424 associated with the adverse-event report 420. An example section can include an introduction section that provides a background section that describes the subject's condition, the treatment being studied, and the context in which the adverse event occurred. A second example section can include clinical-measurement section of the adverse event, including timing (onset, duration), symptoms, and any relevant laboratory or diagnostic findings. A third example section can include a clinical-context section that provides the subject's medical history, concomitant medications, and other factors that might have influenced the occurrence of the adverse event. The clinical-context section can also include any modifications to the treatment, such as dose adjustments, discontinuation, or additional therapies provided in response to the adverse event. Other examples of the sections can include: (i) a narrative section that describes a resolution of the adverse event, including whether the patient recovered, experienced ongoing issues, or had a fatal outcome; (ii) an evaluation section that describes the relationship between the treatment and the adverse event, supported by clinical reasoning and relevant evidence; and (iii) a conclusion section that summarizes the adverse event's significance in the context of the clinical trial or medical treatment, and any recommendations for future monitoring or investigation.

Additionally or alternatively, the one or more sections 424 of the adverse-event report 420 can be generated according to regulatory data associated with one or more regulatory agencies. Such modification to the one or more sections can facilitate regulatory review and approval. In some instances, the one or more sections 424 of the adverse-event report 420 are further processed for formatting, compliance checks, and automated validation to ensure adherence to regulatory standards. The additional processing can not only ensure compliance with regulatory standards but also enhance the overall reliability and credibility of the clinical-trial results. In some instances, the machine-learning model accesses the regulatory data from a retrieval-augmentation generation (RAG) system to generate the one or more sections of the adverse-event report.

3. Output Module

The output module 407 can then cause the one or more sections 424 associated with the adverse-event report to be displayed on the second portion 412 of the user interface of the document-processing application 408. For example, the one or more sections 424 associated with the adverse-event report 420 can be displayed on a main interface of the document-processing application.

In some instances, the input module 404 receives modifications to the one or more sections 424 of the adverse-event report 420. The report-generating application 402 can generate feedback data based on the modifications, in which the feedback data can be used to further train the machine-learning model (e.g., reinforcement learning). The updating of the machine-learning model can thus improve quality and accuracy of the adverse-event report 420, thereby increasing the probability of the reports being accepted by the regulatory agencies. The report-generating application 402 thus allows for multiple iterations of providing feedback to an initial output (i.e., the adverse-event report), thus refining subsequent adverse-event reports based on the feedback until a target output is achieved. The iterative approach facilitates increased efficiency in generating high-quality adverse-event report.

In some instances, the user interface (e.g., the second portion 412 of the user interface) can include one or more user-interface elements that facilitate review of the generated adverse-event report 420 and provide immediate feedback. For example, the feedback data can include text inputted by the users. In some instances, a free text box is provided for detailed feedback. In another example, the feedback can include interacting with a graphical user-interface element that indicates approval or disapproval of the generated content (e.g., clicking a thumbs up/down icon).

In some instances, the feedback data includes one or more modifications to the adverse-event report 420. In some instances, the feedback data further includes an approval or disapproval of the adverse-event report 420. In some instances, the report-generating application provides a content editor to support the one or more modifications. In some instances, another machine-learning model is used to process the feedback data and generate real-time suggestions such as grammar corrections, alternative phrasings, or additional relevant information. Additionally or alternatively, a version-control subsystem can be implemented by the content editor to track changes, thus allowing the users to revert the edited content to previous versions or comparing different iterations of the adverse-event report.

After receiving the feedback data, the adverse-event report generator 422 can adjust one or more parameters of the machine-learning model based on a loss determined between the one or more modifications and corresponding portions of the adverse-event report. The loss can be determined using different loss functions, such as regression, classification, or other specialized tasks. For example, Variational Autoencoder (VAE) loss can be used, in which the VAE loss can be determined using a combination of reconstruction loss and Kullback-Leibler (KL) divergence. The reconstruction loss, typically measured as the Mean Squared Error (MSE) or Binary Cross-Entropy (BCE), can quantify how well the generated data (e.g., the one or more sections 424 of the adverse-event report 420) matches the modified sections of the adverse-event report, encouraging accurate data reconstruction. The KL divergence term measures how closely the learned latent variable distribution approximates the prior distribution, usually a standard normal distribution.

In some instances, the adverse-event report generator 422 adjusts the one or more parameters of the machine-learning model using reinforcement learning. Reinforcement Learning (RL) is a machine learning paradigm where an automated agent learns to make decisions by interacting with the adverse-event report generator 422 to maximize cumulative rewards. The fundamental components of RL include the automated agent, environment, state, action, reward, policy, value function, and Q-value. The automated agent can interact with the adverse-event report generator 422 in a loop, taking actions based on the current policy, observing the resulting state and reward, and updating its policy and value function accordingly.

Examples of RL algorithms include Q-learning, SARSA, Deep Q-Networks (DQN), policy gradient methods, and actor-critic methods. For example, Q-learning can be an off-policy approach, in which the Q-value function is updated using the maximum estimated future rewards. In another example, SARSA is an on-policy method that updates the Q-value function based on the action actually taken by the current policy. DQN can use another neural network to approximate the Q-value function and uses various techniques (e.g., experience replay) to stabilize training. The loss function in DQN is the Mean Squared Error (MSE) between predicted and target Q-values, which is minimized using gradient descent.

As a result, the feedback data can be used for further training and fine-tuning of the machine-learning model to generate future adverse-event reports that accurately correlate the input data (e.g., the clinical-data items associated with the particular subject) with the adverse-event report, including accounting for the contextual data inputted by the users. If the feedback data includes the approval or disapproval of the adverse-event report, the one or more parameters of the machine-learning model are further adjusted based on the approval or disapproval of the adverse-event report.

C. Methods

Figure 5:
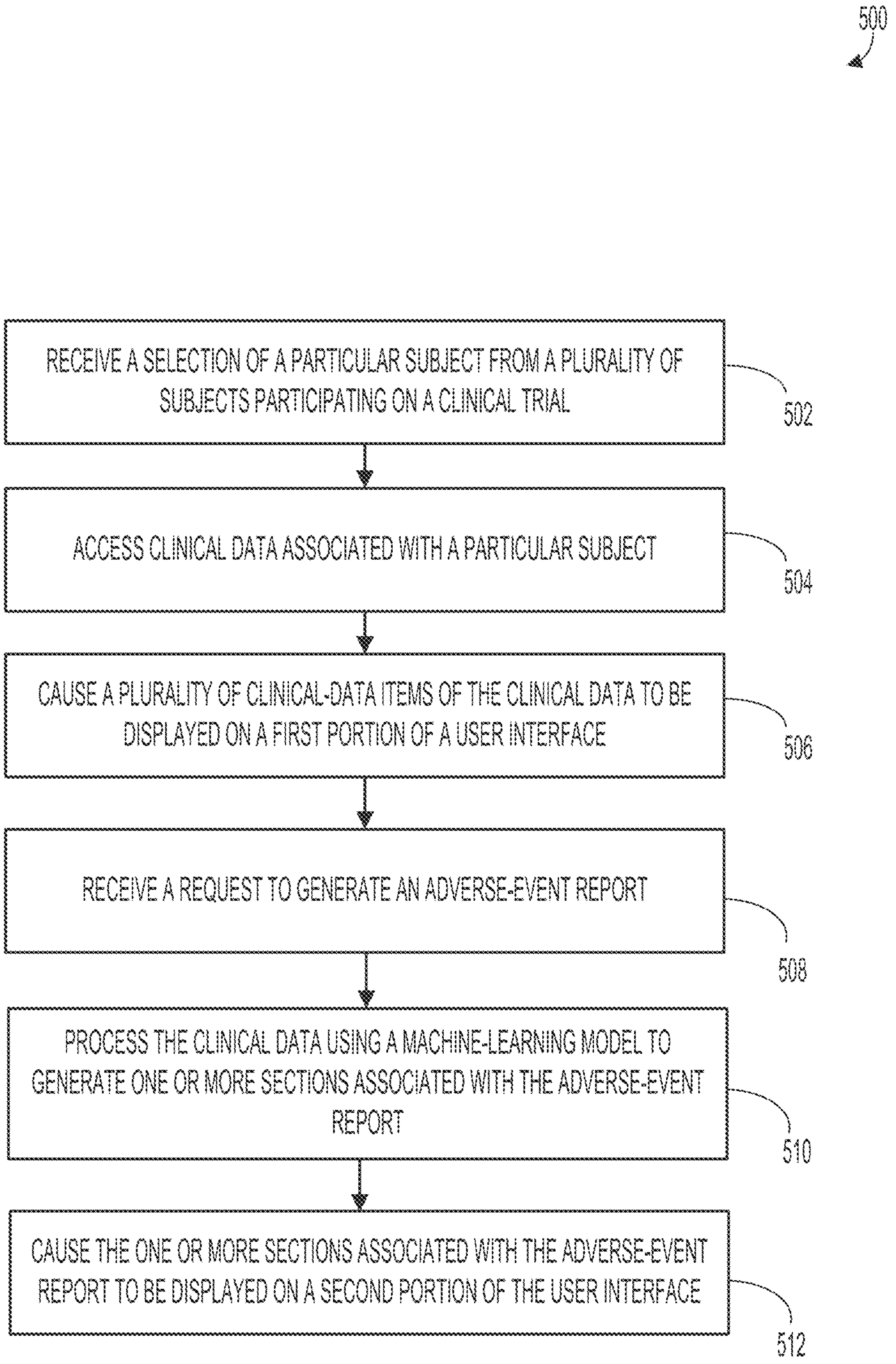
FIG. 5 shows an illustrative example of a process for generating adverse-event reports using machine-learning models, in accordance with some embodiments.

FIG. 5 shows an illustrative example of a process 500 for generating adverse-event reports using machine-learning models, in accordance with some embodiments. For illustrative purposes, the process 500 is described with reference to the components illustrated in FIGS. 1-4, though other implementations are possible. For example, the program code for the report-generating application 402 of FIG. 4, is executed by one or more processing devices to cause a server system (e.g., the computing device 602 of FIG. 6) to perform one or more operations described herein.

At step 502, a report-generating application receives a selection of a particular subject from a plurality of subjects participating on a clinical trial. A plurality of identifiers associated with the plurality of subjects can be displayed on a first portion of a user interface associated with a document-processing application, at which an identifier corresponding to the particular subject can be selected. In some instances, the plurality of identifiers are generated to prevent exposure of the subject's personal identifiable information (PII). For example, the identifier of the particular subject can correspond to "EDB01-001-004-002", which obfuscates the PII of the particular subject.

At step 504, the report-generating application accesses clinical data associated with a particular subject, in which the clinical data includes a plurality of clinical-data items. In some instances, each of the plurality of clinical-data items is accessed from one or more clinical-data sources. The one or more clinical-data sources can include various types of data sources. For example, the one or more clinical-data sources can include an adverse-event data source that identifies the one or more adverse events. The one or more clinical-data items associated with the adverse-event data source can identify demographic data associated with the particular subject. In another example, the one or more clinical-data sources can include concomitant-medications data source that identifies one or more types of medications consumed by the particular subject before or during the clinical trial. In yet another example, the one or more clinical-data sources can include a laboratory-results data source that identifies various clinical results that were measured for the particular subject during the clinical trial.

At step 506, the report-generating application causes the plurality of clinical-data items to be displayed on the first portion of the user interface. For example, the plurality of clinical-data items can be displayed on a task pane of the document-processing application. Task panes can include dockable windows that present the clinical-data items and interact with the user. The task panes can be placed on the right, left, top, or bottom of the Word document. In other examples, the plurality of clinical-data items can also be displayed on a toolbar of the document-processing application and/or content add-ins that facilitate interaction with the clinical-data items and other content presented on the document-processing application. Additionally or alternatively, the first portion can be dialog boxes that require user interaction with the clinical-data items before returning to the user interface.

At step 508, the report-generating application receives a request to generate an adverse-event report. For example, the request can be initiated by interacting with one or more user-interface elements of the extension application associated with the report-generating application. Other examples of user-interactions can be implemented to initiate the request, including but not limited to typing the request, swiping, tapping the user-interface element, hovering over the user-interface element, and double-clicking the user-interface element.

As described herein, the adverse-event report can include a comprehensive description of one or more adverse medical events, in which the report can be included in clinical study reports, regulatory submissions, and pharmacovigilance documents. In some instances, the adverse-event report can include a chronological description of one or more adverse events associated with the particular subject, in which the one or more adverse events were identified during participation of the particular subject for the clinical trial.

At step 510, the report-generating application processes the clinical data using a machine-learning model to generate one or more sections associated with the adverse-event report. The machine-learning model can be trained using a training dataset that includes previous adverse-event reports associated with other clinical trials. In some instances, the one or more sections of the adverse-event report can include an electronic link, in which the electronic link identifies a corresponding clinical-data item from the first portion of the user interface. In some instances, the one or more sections of the adverse-event report includes one or more empty data fields.

The machine-learning model can be a natural-language processing model trained using the previous input data and corresponding adverse-event reports generating using the previous input data. Examples of the machine-learning model can include algorithms such as k-means clustering algorithms, fuzzy c-means (FCM) algorithms, expectation-maximization (EM) algorithms, hierarchical clustering algorithms, and density-based spatial clustering of applications with noise (DBSCAN) algorithms, in which the algorithms can be trained using unsupervised learning. Other examples of the machine-learning model can include, but are not limited to, genetic algorithms, backpropagation, reinforcement learning, decision trees, linear classification, artificial neural networks, anomaly detection, and such. In yet other examples, the machine-learning model may include regression analysis, dimensionality reduction, metalearning, reinforcement learning, deep learning, and other such algorithms and/or methods.

In some instances, the machine-learning model is a transformer model (e.g., a large-language model (LLM)) obtained from a models database. In some instances, the machine-learning model is trained using self-supervised learning based on a large corpus of text data, such that the machine-learning model can generate the adverse-event report. In addition to training the model, various prompts can be used for prompt engineering of the machine-learning model for generating the adverse-event report. Examples of the machine-learning model can include, but are not limited to, BERT model, Claude LLM, Falcon 40B, Ernic, GPT-3, GPT-3.5, GPT 4, Lamda, and Llama.

Additionally or alternatively, regulatory data can be processed using the machine-learning model to supplement the one or more sections of adverse-event report. In some instances, the machine-learning model accesses the regulatory data from a retrieval-augmentation generation (RAG) system to generate the one or more sections of the adverse-event report. For example, the regulatory data can include guidelines from regulatory bodies such as the Food and Drug Administration (FDA) and the European Medicines Agency (EMA).

At step 512, the report-generating application causes the one or more sections associated with the adverse-event report to be displayed on a second portion of the user interface of the document-processing application. For example, the one or more sections associated with the adverse-event report can be displayed on a main interface of the document-processing application. In some instances, the report-generating application receives modifications to the one or more sections of the adverse-event report. The report-generating application can generate feedback data based on the modifications, in which the feedback data can be used to further train the machine-learning model (e.g., reinforcement learning). Process 500 terminates thereafter.

II. Example Systems

Figure 6:
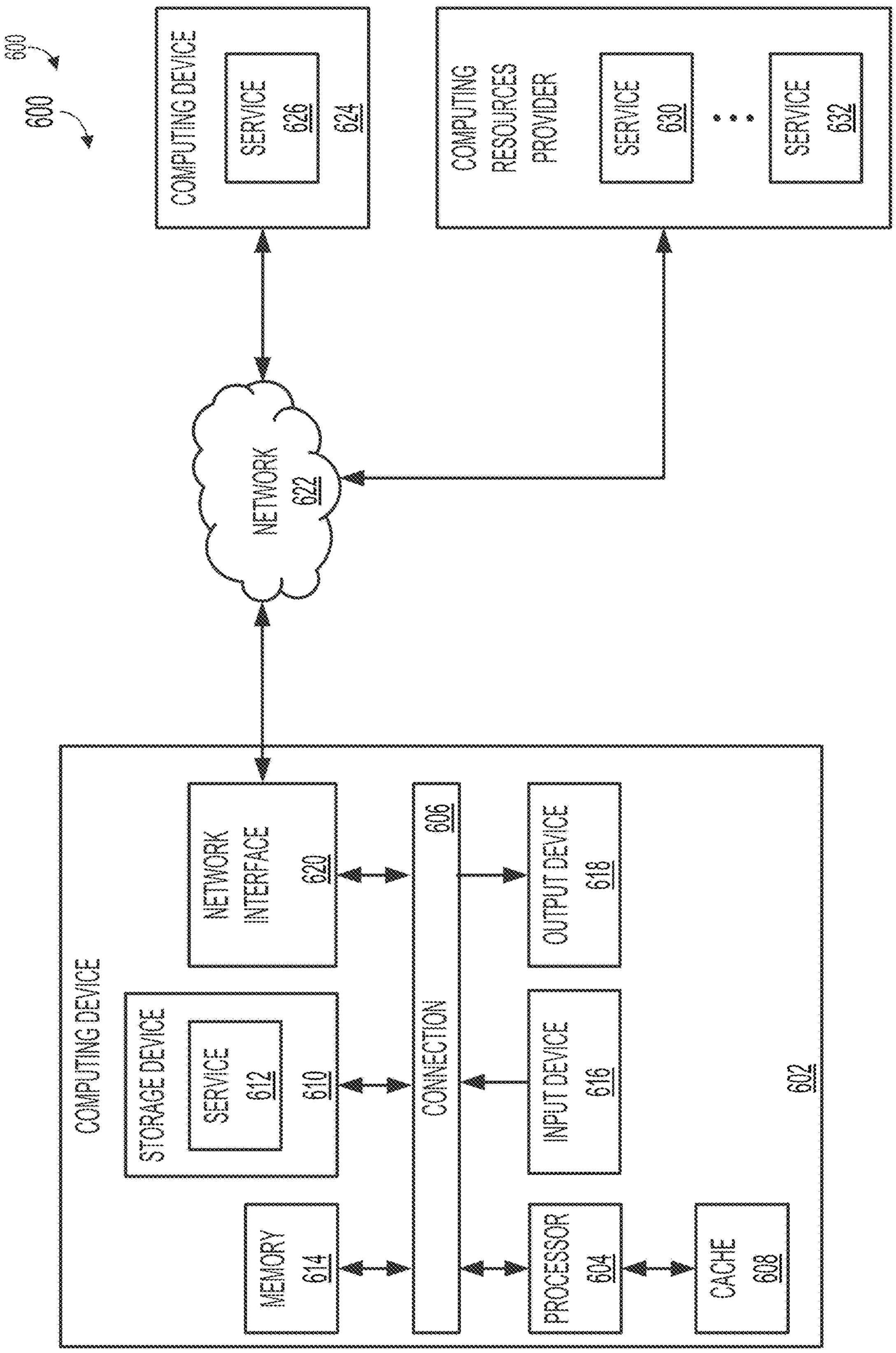
FIG. 6 shows a computing system architecture including various components in electrical communication with each other using a connection in accordance with various embodiments.

FIG. 6 illustrates a computing system architecture 600, including various components in electrical communication with each other, in accordance with some embodiments. The example computing system architecture 600 illustrated in FIG. 6 includes a computing device 602, which has various components in electrical communication with each other using a connection 606, such as a bus, in accordance with some implementations. The example computing system architecture 600 includes a processing unit 604 that is in electrical communication with various system components, using the connection 606, and including the system memory 614. In some embodiments, the system memory 614 includes read-only memory (ROM), random-access memory (RAM), and other such memory technologies including, but not limited to, those described herein. In some embodiments, the example computing system architecture 600 includes a cache 608 of high-speed memory connected directly with, in close proximity to, or integrated as part of the processor 604. The system architecture 600 can copy data from the memory 614 and/or the storage device 610 to the cache 608 for quick access by the processor 604. In this way, the cache 608 can provide a performance boost that decreases or eliminates processor delays in the processor 604 due to waiting for data. Using modules, methods and services such as those described herein, the processor 604 can be configured to perform various actions. In some embodiments, the cache 608 may include multiple types of cache including, for example, level one (L1) and level two (L2) cache. The memory 614 may be referred to herein as system memory or computer system memory. The memory 614 may include, at various times, elements of an operating system, one or more applications, data associated with the operating system or the one or more applications, or other such data associated with the computing device 602.

Other system memory 614 can be available for use as well. The memory 614 can include multiple different types of memory with different performance characteristics. The processor 604 can include any general purpose processor and one or more hardware or software services, such as service 612 stored in storage device 610, configured to control the processor 604 as well as a special-purpose processor where software instructions are incorporated into the actual processor design. The processor 604 can be a completely self-contained computing system, containing multiple cores or processors, connectors (e.g., buses), memory, memory controllers, caches, etc. In some embodiments, such a self-contained computing system with multiple cores is symmetric. In some embodiments, such a self-contained computing system with multiple cores is asymmetric. In some embodiments, the processor 604 can be a microprocessor, a microcontroller, a digital signal processor ("DSP"), or a combination of these and/or other types of processors. In some embodiments, the processor 604 can include multiple elements such as a core, one or more registers, and one or more processing units such as an arithmetic logic unit (ALU), a floating point unit (FPU), a graphics processing unit (GPU), a physics processing unit (PPU), a digital system processing (DSP) unit, or combinations of these and/or other such processing units.

To enable user interaction with the computing system architecture 600, an input device 616 can represent any number of input mechanisms, such as a microphone for speech, a touch-sensitive screen for gesture or graphical input, keyboard, mouse, motion input, pen, and other such input devices. An output device 618 can also be one or more of a number of output mechanisms known to those of skill in the art including, but not limited to, monitors, speakers, printers, haptic devices, and other such output devices. In some instances, multimodal systems can enable a user to provide multiple types of input to communicate with the computing system architecture 600. In some embodiments, the input device 616 and/or the output device 618 can be coupled to the computing device 602 using a remote connection device such as, for example, a communication interface such as the network interface 620 described herein. In such embodiments, the communication interface can govern and manage the input and output received from the attached input device 616 and/or output device 618. As may be contemplated, there is no restriction on operating on any particular hardware arrangement and accordingly the basic features here may easily be substituted for other hardware, software, or firmware arrangements as they are developed.

In some embodiments, the storage device 610 can be described as non-volatile storage or non-volatile memory. Such non-volatile memory or non-volatile storage can be a hard disk or other types of computer readable media which can store data that are accessible by a computer, such as magnetic cassettes, flash memory cards, solid state memory devices, digital versatile disks, cartridges, RAM, ROM, and hybrids thereof.

As described above, the storage device 610 can include hardware and/or software services such as service 612 that can control or configure the processor 604 to perform one or more functions including, but not limited to, the methods, processes, functions, systems, and services described herein in various embodiments. In some embodiments, the hardware or software services can be implemented as modules. As illustrated in example computing system architecture 600, the storage device 610 can be connected to other parts of the computing device 602 using the system connection 606. In some embodiments, a hardware service or hardware module such as service 612, that performs a function can include a software component stored in a non-transitory computer-readable medium that, in connection with the necessary hardware components, such as the processor 604, connection 606, cache 608, storage device 610, memory 614, input device 616, output device 618, and so forth, can carry out the functions such as those described herein.

The disclosed systems and service of a report-generating application (e.g., the report-generating application described herein at least in connection with FIG. 3) can be performed using a computing system such as the example computing system illustrated in FIG. 6, using one or more components of the example computing system architecture 600. An example computing system can include a processor (e.g., a central processing unit), memory, non-volatile memory, and an interface device. The memory may store data and/or and one or more code sets, software, scripts, etc. The components of the computer system can be coupled together via a bus or through some other known or convenient device.

In some embodiments, the processor can be configured to carry out some or all of methods and systems for generating adverse-event reports associated with the report-generating application (e.g., the report-generating application 302 described herein at least in connection with FIG. 3) described herein by, for example, executing code using a processor such as processor 604 wherein the code is stored in memory such as memory 614 as described herein. One or more of a user device, a provider server or system, a database system, or other such devices, services, or systems may include some or all of the components of the computing system such as the example computing system illustrated in FIG. 6, using one or more components of the example computing system architecture 600 illustrated herein. As may be contemplated, variations on such systems can be considered as within the scope of the present disclosure.

This disclosure contemplates the computer system taking any suitable physical form. As example and not by way of limitation, the computer system can be an embedded computer system, a system-on-chip (SOC), a single-board computer system (SBC) (such as, for example, a computer-on-module (COM) or system-on-module (SOM)), a desktop computer system, a laptop or notebook computer system, a tablet computer system, a wearable computer system or interface, an interactive kiosk, a mainframe, a mesh of computer systems, a mobile telephone, a personal digital assistant (PDA), a server, or a combination of two or more of these. Where appropriate, the computer system may include one or more computer systems; be unitary or distributed; span multiple locations; span multiple machines; and/or reside in a cloud computing system which may include one or more cloud components in one or more networks as described herein in association with the computing resources provider 628. Where appropriate, one or more computer systems may perform without substantial spatial or temporal limitation one or more steps of one or more methods described or illustrated herein. As an example and not by way of limitation, one or more computer systems may perform in real time or in batch mode one or more steps of one or more methods described or illustrated herein. One or more computer systems may perform at different times or at different locations one or more steps of one or more methods described or illustrated herein, where appropriate.

The processor 604 can be a conventional microprocessor such as an Intel® microprocessor, an AMD® microprocessor, a Motorola® microprocessor, or other such microprocessors. One of skill in the relevant art will recognize that the terms "machine-readable (storage) medium" or "computer-readable (storage) medium" include any type of device that is accessible by the processor.

The memory 614 can be coupled to the processor 604 by, for example, a connector such as connector 606, or a bus. As used herein, a connector or bus such as connector 606 is a communications system that transfers data between components within the computing device 602 and may, in some embodiments, be used to transfer data between computing devices. The connector 606 can be a data bus, a memory bus, a system bus, or other such data transfer mechanism. Examples of such connectors include, but are not limited to, an industry standard architecture (ISA" bus, an extended ISA (EISA) bus, a parallel AT attachment (PATA" bus (e.g., an integrated drive electronics (IDE) or an extended IDE (EIDE) bus), or the various types of parallel component interconnect (PCI) buses (e.g., PCI, PCIe, PCI-104, etc.).

The memory 614 can include RAM including, but not limited to, dynamic RAM (DRAM), static RAM (SRAM), synchronous dynamic RAM (SDRAM), non-volatile random access memory (NVRAM), and other types of RAM. The DRAM may include error-correcting code (EEC). The memory can also include ROM including, but not limited to, programmable ROM (PROM), erasable and programmable ROM (EPROM), electronically erasable and programmable ROM (EEPROM), Flash Memory, masked ROM (MROM), and other types or ROM. The memory 614 can also include magnetic or optical data storage media including read-only (e.g., CD ROM and DVD ROM) or otherwise (e.g., CD or DVD). The memory can be local, remote, or distributed.

As described above, the connector 606 (or bus) can also couple the processor 604 to the storage device 610, which may include non-volatile memory or storage and which may also include a drive unit. In some embodiments, the non-volatile memory or storage is a magnetic floppy or hard disk, a magnetic-optical disk, an optical disk, a ROM (e.g., a CD-ROM, DVD-ROM, EPROM, or EEPROM), a magnetic or optical card, or another form of storage for data. Some of this data may be written, by a direct memory access process, into memory during execution of software in a computer system. The non-volatile memory or storage can be local, remote, or distributed. In some embodiments, the non-volatile memory or storage is optional. As may be contemplated, a computing system can be created with all applicable data available in memory. A typical computer system will usually include at least one processor, memory, and a device (e.g., a bus) coupling the memory to the processor.

Software and/or data associated with software can be stored in the non-volatile memory and/or the drive unit. In some embodiments (e.g., for large programs) it may not be possible to store the entire program and/or data in the memory at any one time. In such embodiments, the program and/or data can be moved in and out of memory from, for example, an additional storage device such as storage device 610. Nevertheless, it should be understood that for software to run, if necessary, it is moved to a computer readable location appropriate for processing, and for illustrative purposes, that location is referred to as the memory herein. Even when software is moved to the memory for execution, the processor can make use of hardware registers to store values associated with the software, and local cache that, ideally, serves to speed up execution. As used herein, a software program is assumed to be stored at any known or convenient location (from non-volatile storage to hardware registers), when the software program is referred to as "implemented in a computer-readable medium." A processor is considered to be "configured to execute a program" when at least one value associated with the program is stored in a register readable by the processor.

The connection 606 can also couple the processor 604 to a network interface device such as the network interface 620. The interface can include one or more of a modem or other such network interfaces including, but not limited to those described herein. It will be appreciated that the network interface 620 may be considered to be part of the computing device 602 or may be separate from the computing device 602. The network interface 620 can include one or more of an analog modem, Integrated Services Digital Network (ISDN) modem, cable modem, token ring interface, satellite transmission interface, or other interfaces for coupling a computer system to other computer systems. In some embodiments, the network interface 620 can include one or more input and/or output (I/O) devices. The I/O devices can include, by way of example but not limitation, input devices such as input device 616 and/or output devices such as output device 618. For example, the network interface 620 may include a keyboard, a mouse, a printer, a scanner, a display device, and other such components. Other examples of input devices and output devices are described herein. In some embodiments, a communication interface device can be implemented as a complete and separate computing device.

In operation, the computer system can be controlled by operating system software that includes a file management system, such as a disk operating system. One example of operating system software with associated file management system software is the family of Windows® operating systems and their associated file management systems. Another example of operating system software with its associated file management system software is the Linux™ operating system and its associated file management system including, but not limited to, the various types and implementations of the Linux® operating system and their associated file management systems. The file management system can be stored in the non-volatile memory and/or drive unit and can cause the processor to execute the various acts required by the operating system to input and output data and to store data in the memory, including storing files on the non-volatile memory and/or drive unit. As may be contemplated, other types of operating systems such as, for example, MacOS®, other types of UNIX® operating systems (e.g., BSD™ and descendants, Xenix™, SunOS™, HP-UX®, etc.), mobile operating systems (e.g., iOS® and variants, Chrome®, Ubuntu Touch®, watchOS®, Windows 10 Mobile®, the Blackberry® OS, etc.), and real-time operating systems (e.g., Vx Works®, QNX®, cCos®, RTLinux®, etc.) may be considered as within the scope of the present disclosure. As may be contemplated, the names of operating systems, mobile operating systems, real-time operating systems, languages, and devices, listed herein may be registered trademarks, service marks, or designs of various associated entities.

In some embodiments, the computing device 602 can be connected to one or more additional computing devices such as computing device 624 via a network 622 using a connection such as the network interface 620. In such embodiments, the computing device 624 may execute one or more services 626 to perform one or more functions under the control of, or on behalf of, programs and/or services operating on computing device 602. In some embodiments, a computing device such as computing device 624 may include one or more of the types of components as described in connection with computing device 602 including, but not limited to, a processor such as processor 604, a connection such as connection 606, a cache such as cache 608, a storage device such as storage device 610, memory such as memory 614, an input device such as input device 616, and an output device such as output device 618. In such embodiments, the computing device 624 can carry out the functions such as those described herein in connection with computing device 602. In some embodiments, the computing device 602 can be connected to a plurality of computing devices such as computing device 624, each of which may also be connected to a plurality of computing devices such as computing device 624. Such an embodiment may be referred to herein as a distributed computing environment.

The network 622 can be any network including an internet, an intranet, an extranet, a cellular network, a Wi-Fi network, a local area network (LAN), a wide area network (WAN), a satellite network, a Bluetooth® network, a virtual private network (VPN), a public switched telephone network, an infrared (IR) network, an internet of things (IoT network) or any other such network or combination of networks. Communications via the network 622 can be wired connections, wireless connections, or combinations thereof. Communications via the network 622 can be made via a variety of communications protocols including, but not limited to, Transmission Control Protocol/Internet Protocol (TCP/IP), User Datagram Protocol (UDP), protocols in various layers of the Open System Interconnection (OSI) model, File Transfer Protocol (FTP), Universal Plug and Play (UPnP), Network File System (NFS), Server Message Block (SMB), Common Internet File System (CIFS), and other such communications protocols.

Communications over the network 622, within the computing device 602, within the computing device 624, or within the computing resources provider 628 can include information, which also may be referred to herein as content. The information may include text, graphics, audio, video, haptics, and/or any other information that can be provided to a user of the computing device such as the computing device 602. In some embodiments, the information can be delivered using a transfer protocol such as Hypertext Markup Language (HTML), Extensible Markup Language (XML), JavaScript®, Cascading Style Sheets (CSS), JavaScript® Object Notation (JSON), and other such protocols and/or structured languages. The information may first be processed by the computing device 602 and presented to a user of the computing device 602 using forms that are perceptible via sight, sound, smell, taste, touch, or other such mechanisms. In some embodiments, communications over the network 622 can be received and/or processed by a computing device configured as a server. Such communications can be sent and received using PHP: Hypertext Preprocessor ("PHP"), Python™, Ruby, Perl® and variants, Java®, HTML, XML, or another such server-side processing language.

In some embodiments, the computing device 602 and/or the computing device 624 can be connected to a computing resources provider 628 via the network 622 using a network interface such as those described herein (e.g. network interface 620). In such embodiments, one or more systems (e.g., service 630 and service 632) hosted within the computing resources provider 628 (also referred to herein as within "a computing resources provider environment") may execute one or more services to perform one or more functions under the control of, or on behalf of, programs and/or services operating on computing device 602 and/or computing device 624. Systems such as service 630 and service 632 may include one or more computing devices such as those described herein to execute computer code to perform the one or more functions under the control of, or on behalf of, programs and/or services operating on computing device 602 and/or computing device 624.

For example, the computing resources provider 628 may provide a service, operating on service 630 to store data for the computing device 602 when, for example, the amount of data that the computing device 602 exceeds the capacity of storage device 610. In another example, the computing resources provider 628 may provide a service to first instantiate a virtual machine (VM) on service 632, use that VM to access the data stored on service 632, perform one or more operations on that data, and provide a result of those one or more operations to the computing device 602. Such operations (e.g., data storage and VM instantiation) may be referred to herein as operating "in the cloud," "within a cloud computing environment," or "within a hosted virtual machine environment," and the computing resources provider 628 may also be referred to herein as "the cloud." Examples of such computing resources providers include, but are not limited to Amazon® Web Services (AWS®), Microsoft's Azure®, IBM Cloud®, Google Cloud®, Oracle Cloud® etc.

Services provided by a computing resources provider 628 include, but are not limited to, data analytics, data storage, archival storage, big data storage, virtual computing (including various scalable VM architectures), blockchain services, containers (e.g., application encapsulation), database services, development environments (including sandbox development environments), e-commerce solutions, game services, media and content management services, security services, server-less hosting, virtual reality (VR) systems, and augmented reality (AR) systems. Various techniques to facilitate such services include, but are not be limited to, virtual machines, virtual storage, database services, system schedulers (e.g., hypervisors), resource management systems, various types of short-term, mid-term, long-term, and archival storage devices, etc.

As may be contemplated, the systems such as service 630 and service 632 may implement versions of various services (e.g., the service 612 or the service 626) on behalf of, or under the control of, computing device 602 and/or computing device 624. Such implemented versions of various services may involve one or more virtualization techniques so that, for example, it may appear to a user of computing device 602 that the service 612 is executing on the computing device 602 when the service is executing on, for example, service 630. As may also be contemplated, the various services operating within the computing resources provider 628 environment may be distributed among various systems within the environment as well as partially distributed onto computing device 624 and/or computing device 602.

Client devices, user devices, computer resources provider devices, network devices, and other devices can be computing systems that include one or more integrated circuits, input devices, output devices, data storage devices, and/or network interfaces, among other things. The integrated circuits can include, for example, one or more processors, volatile memory, and/or non-volatile memory, among other things such as those described herein. The input devices can include, for example, a keyboard, a mouse, a key pad, a touch interface, a microphone, a camera, and/or other types of input devices including, but not limited to, those described herein. The output devices can include, for example, a display screen, a speaker, a haptic feedback system, a printer, and/or other types of output devices including, but not limited to, those described herein. A data storage device, such as a hard drive or flash memory, can enable the computing device to temporarily or permanently store data. A network interface, such as a wireless or wired interface, can enable the computing device to communicate with a network. Examples of computing devices (e.g., the computing device 602) include, but is not limited to, desktop computers, laptop computers, server computers, hand-held computers, tablets, smart phones, personal digital assistants, digital home assistants, wearable devices, smart devices, and combinations of these and/or other such computing devices as well as machines and apparatuses in which a computing device has been incorporated and/or virtually implemented.

The techniques described herein may also be implemented in electronic hardware, computer software, firmware, or any combination thereof. Such techniques may be implemented in any of a variety of devices such as general purpose computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as that described herein. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices (e.g., a combination of a DSP and a microprocessor), a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for implementing a suspended database update system.

As used herein, the term "machine-readable media" and equivalent terms "machine-readable storage media," "computer-readable media," and "computer-readable storage media" refer to media that includes, but is not limited to, portable or non-portable storage devices, optical storage devices, removable or non-removable storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), solid state drives (SSD), flash memory, memory or memory devices.

A machine-readable medium or machine-readable storage medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like. Further examples of machine-readable storage media, machine-readable media, or computer-readable (storage) media include but are not limited to recordable type media such as volatile and non-volatile memory devices, floppy and other removable disks, hard disk drives, optical disks (e.g., CDs, DVDs, etc.), among others, and transmission type media such as digital and analog communication links.

As may be contemplated, while examples herein may illustrate or refer to a machine-readable medium or machine-readable storage medium as a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding, or carrying a set of instructions for execution by the system and that cause the system to perform any one or more of the methodologies or modules of disclosed herein.

Some portions of the detailed description herein may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as “processing” or “computing” or “calculating” or “determining” or “displaying” or “generating” or the like, refer to the action and processes of a computer system, or similar electronic computing device, that manipulates and transforms data represented as physical (electronic) quantities within registers and memories of the computer system into other data similarly represented as physical quantities within the computer system memories or registers or other such information storage, transmission or display devices.

It is also noted that individual implementations may be described as a process which is depicted as a flowchart, a flow diagram, a data flow diagram, a structure diagram, or a block diagram (e.g., the example process 500 of FIG. 5). Although a flowchart, a flow diagram, a data flow diagram, a structure diagram, or a block diagram may describe the operations as a sequential process, many of the operations can be performed in parallel or concurrently. In addition, the order of the operations may be re-arranged. A process illustrated in a figure is terminated when its operations are completed, but could have additional steps not included in the figure. A process may correspond to a method, a function, a procedure, a subroutine, a subprogram, etc. When a process corresponds to a function, its termination can correspond to a return of the function to the calling function or the main function.

In some embodiments, one or more implementations of an algorithm such as those described herein may be implemented using a machine learning or artificial intelligence algorithm. Such a machine learning or artificial intelligence algorithm may be trained using supervised, unsupervised, reinforcement, or other such training techniques. For example, a set of data may be analyzed using one of a variety of machine learning algorithms to identify correlations between different elements of the set of data without supervision and feedback (e.g., an unsupervised training technique). A machine learning data analysis algorithm may also be trained using sample or live data to identify potential correlations. Such algorithms may include k-means clustering algorithms, fuzzy c-means (FCM) algorithms, expectation-maximization (EM) algorithms, hierarchical clustering algorithms, density-based spatial clustering of applications with noise (DBSCAN) algorithms, and the like. Other examples of machine learning or artificial intelligence algorithms include, but are not limited to, genetic algorithms, backpropagation, reinforcement learning, decision trees, liner classification, artificial neural networks, anomaly detection, and such. More generally, machine learning or artificial intelligence methods may include regression analysis, dimensionality reduction, metalearning, reinforcement learning, deep learning, and other such algorithms and/or methods. As may be contemplated, the terms “machine learning” and “artificial intelligence” are frequently used interchangeably due to the degree of overlap between these fields and many of the disclosed techniques and algorithms have similar approaches.

As an example of a supervised training technique, a set of data can be selected for training of the machine learning model to facilitate identification of correlations between members of the set of data. The machine learning model may be evaluated to determine, based on the sample inputs supplied to the machine learning model, whether the machine learning model is producing accurate correlations between members of the set of data. Based on this evaluation, the machine learning model may be modified to increase the likelihood of the machine learning model identifying the desired correlations. The machine learning model may further be dynamically trained by soliciting feedback from users of a system as to the efficacy of correlations provided by the machine learning algorithm or artificial intelligence algorithm (i.e., the supervision). The machine learning algorithm or artificial intelligence may use this feedback to improve the algorithm for generating correlations (e.g., the feedback may be used to further train the machine learning algorithm or artificial intelligence to provide more accurate correlations).

The various examples of flowcharts, flow diagrams, data flow diagrams, structure diagrams, or block diagrams discussed herein may further be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a computer-readable or machine-readable storage medium (e.g., a medium for storing program code or code segments) such as those described herein. A processor(s), implemented in an integrated circuit, may perform the necessary tasks.

The various illustrative logical blocks, modules, circuits, and algorithm steps described in connection with the implementations disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

It should be noted, however, that the algorithms and displays presented herein are not inherently related to any particular computer or other apparatus. Various general purpose systems may be used with programs in accordance with the teachings herein, or it may prove convenient to construct more specialized apparatus to perform the methods of some examples. The required structure for a variety of these systems will appear from the description below. In addition, the techniques are not described with reference to any particular programming language, and various examples may thus be implemented using a variety of programming languages.

In various implementations, the system operates as a standalone device or may be connected (e.g., networked) to other systems. In a networked deployment, the system may operate in the capacity of a server or a client system in a client-server network environment, or as a peer system in a peer-to-peer (or distributed) network environment.

The system may be a server computer, a client computer, a personal computer (PC), a tablet PC (e.g., an iPad®, a Microsoft Surface®, a Chromebook®, etc.), a laptop computer, a set-top box (STB), a personal digital assistants (PDA), a mobile device (e.g., a cellular telephone, an iPhone®, and Android® device, a Blackberry®, etc.), a wearable device, an embedded computer system, an electronic book reader, a processor, a telephone, a web appliance, a network router, switch or bridge, or any system capable of executing a set of instructions (sequential or otherwise) that specify actions to be taken by that system. The system may also be a virtual system such as a virtual version of one of the aforementioned devices that may be hosted on another computer device such as the computer device 602.

In general, the routines executed to implement the implementations of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while examples have been described in the context of fully functioning computers and computer systems, those skilled in the art will appreciate that the various examples are capable of being distributed as a program object in a variety of forms, and that the disclosure applies equally regardless of the particular type of machine or computer-readable media used to actually effect the distribution.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and storage of charge or a release of stored charge. Likewise, in other memory devices, a change of state may comprise a physical change or transformation in magnetic orientation or a physical change or transformation in molecular structure, such as from crystalline to amorphous or vice versa. The foregoing is not intended to be an exhaustive list of all examples in which a change in state for a binary one to a binary zero or vice-versa in a memory device may comprise a transformation, such as a physical transformation. Rather, the foregoing is intended as illustrative examples.

A storage medium typically may be non-transitory or comprise a non-transitory device. In this context, a non-transitory storage medium may include a device that is tangible, meaning that the device has a concrete physical form, although the device may change its physical state. Thus, for example, non-transitory refers to a device remaining tangible despite this change in state.

The above description and drawings are illustrative and are not to be construed as limiting or restricting the subject matter to the precise forms disclosed. Persons skilled in the relevant art can appreciate that many modifications and variations are possible in light of the above disclosure and may be made thereto without departing from the broader scope of the embodiments as set forth herein. Numerous specific details are described to provide a thorough understanding of the disclosure. However, in certain instances, well-known or conventional details are not described in order to avoid obscuring the description.

As used herein, the terms "connected," "coupled," or any variant thereof when applying to modules of a system, means any connection or coupling, either direct or indirect, between two or more elements; the coupling of connection between the elements can be physical, logical, or any combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, or any combination of the items in the list.

As used herein, the terms "a" and "an" and "the" and other such singular referents are to be construed to include both the singular and the plural, unless otherwise indicated herein or clearly contradicted by context.

As used herein, the terms "comprising," "having," "including," and "containing" are to be construed as open-ended (e.g., "including" is to be construed as "including, but not limited to"), unless otherwise indicated or clearly contradicted by context.

As used herein, the recitation of ranges of values is intended to serve as a shorthand method of referring individually to each separate value falling within the range, unless otherwise indicated or clearly contradicted by context. Accordingly, each separate value of the range is incorporated into the specification as if it were individually recited herein.

As used herein, use of the terms "set" (e.g., "a set of items") and "subset" (e.g., "a subset of the set of items") is to be construed as a nonempty collection including one or more members unless otherwise indicated or clearly contradicted by context. Furthermore, unless otherwise indicated or clearly contradicted by context, the term "subset" of a corresponding set does not necessarily denote a proper subset of the corresponding set but that the subset and the set may include the same elements (i.e., the set and the subset may be the same).

As used herein, use of conjunctive language such as "at least one of A, B, and C" is to be construed as indicating one or more of A, B, and C (e.g., any one of the following nonempty subsets of the set {A, B, C}, namely: {A}, {B}, {C}, {A, B}, {A, C}, {B, C}, or {A, B, C}) unless otherwise indicated or clearly contradicted by context. Accordingly, conjunctive language such as "as least one of A, B, and C" does not imply a requirement for at least one of A, at least one of B, and at least one of C.

As used herein, the use of examples or exemplary language (e.g., "such as" or "as an example") is intended to more clearly illustrate embodiments and does not impose a limitation on the scope unless otherwise claimed. Such language in the specification should not be construed as indicating any non-claimed element is required for the practice of the embodiments described and claimed in the present disclosure.

As used herein, where components are described as being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

Those of skill in the art will appreciate that the disclosed subject matter may be embodied in other forms and manners not shown below. It is understood that the use of relational terms, if any, such as first, second, top and bottom, and the like are used solely for distinguishing one entity or action from another, without necessarily requiring or implying any such actual relationship or order between such entities or actions.

While processes or blocks are presented in a given order, alternative implementations may perform routines having steps, or employ systems having blocks, in a different order, and some processes or blocks may be deleted, moved, added, subdivided, substituted, combined, and/or modified to provide alternative or sub combinations. Each of these processes or blocks may be implemented in a variety of different ways. Also, while processes or blocks are at times shown as being performed in series, these processes or blocks may instead be performed in parallel, or may be performed at different times. Further any specific numbers noted herein are only examples: alternative implementations may employ differing values or ranges.

The teachings of the disclosure provided herein can be applied to other systems, not necessarily the system described above. The elements and acts of the various examples described above can be combined to provide further examples.

Any patents and applications and other references noted above, including any that may be listed in accompanying filing papers, are incorporated herein by reference. Aspects of the disclosure can be modified, if necessary, to employ the systems, functions, and concepts of the various references described above to provide yet further examples of the disclosure.

These and other changes can be made to the disclosure in light of the above Detailed Description. While the above description describes certain examples, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific implementations disclosed in the specification, unless the above Detailed Description section explicitly defines such terms. Accordingly, the actual scope of the disclosure encompasses not only the disclosed implementations, but also all equivalent ways of practicing or implementing the disclosure under the claims.

While certain aspects of the disclosure are presented below in certain claim forms, the inventors contemplate the various aspects of the disclosure in any number of claim forms. Any claims intended to be treated under 45 U.S.C. § 112(f) will begin with the words "means for". Accordingly, the applicant reserves the right to add additional claims after filing the application to pursue such additional claim forms for other aspects of the disclosure.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms may be highlighted, for example using capitalization, italics, and/or quotation marks. The use of highlighting has no influence on the scope and meaning of a term; the scope and meaning of a term is the same, in the same context, whether or not it is highlighted. It will be appreciated that same element can be described in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various examples given in this specification.

Without intent to further limit the scope of the disclosure, examples of instruments, apparatus, methods and their related results according to the examples of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

Some portions of this description describe examples in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In some examples, a software module is implemented with a computer program object comprising a computer-readable medium containing computer program code, which can be executed by a computer processor for performing any or all of the steps, operations, or processes described.

Examples may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Examples may also relate to an object that is produced by a computing process described herein. Such an object may comprise information resulting from a computing process, where the information is stored on a non-transitory, tangible computer readable storage medium and may include any implementation of a computer program object or other data combination described herein.

The language used in the specification has been principally selected for readability and instructional purposes, and it may not have been selected to delineate or circumscribe the subject matter. It is therefore intended that the scope of this disclosure be limited not by this detailed description, but rather by any claims that issue on an application based hereon. Accordingly, the disclosure of the examples is intended to be illustrative, but not limiting, of the scope of the subject matter, which is set forth in the following claims.

Specific details were given in the preceding description to provide a thorough understanding of various implementations of systems and components for a contextual connection system. It will be understood by one of ordinary skill in the art, however, that the implementations described above may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated. It is intended that the scope of the technology be defined by the claim.

What is claimed is:

1. A computer-implemented method comprising:

receiving a selection of a particular subject from a plurality of subjects participating on a clinical trial, wherein a plurality of identifiers associated with the plurality of subjects are displayed on a first portion of a user interface associated with a document-processing application, and wherein selecting the particular subject includes selecting an identifier corresponding to the particular subject;

accessing clinical data associated with a particular subject, wherein the clinical data includes a plurality of clinical-data items, wherein each of the plurality of clinical-data items is accessed from one or more clinical-data sources;

causing the plurality of clinical-data items to be displayed on the first portion of the user interface;

receiving a request to generate an adverse-event report, wherein the adverse-event report includes a chronological description of one or more adverse events associated with the particular subject, and wherein the one or more adverse events were identified during participation of the particular subject for the clinical trial;

processing the clinical data using a machine-learning model to generate one or more sections associated with the adverse-event report, wherein the machine-learning model was trained using a training dataset that includes previous adverse-event reports associated with other clinical trials; and causing the one or more sections associated with the adverse-event report to be displayed on a second portion of the user interface of the document-processing application.

2. The computer-implemented method of claim 1, wherein the one or more clinical-data sources include an adverse-event data source that identifies the one or more adverse events, and wherein one or more clinical-data items associated with the adverse-event data source identify demographic data associated with the particular subject.

3. The computer-implemented method of claim 1, wherein the one or more clinical-data sources include concomitant-medications data source that identifies one or more types of medications consumed by the particular subject before or during the clinical trial.

4. The computer-implemented method of claim 1, wherein the one or more clinical-data sources include a laboratory-results data source that identifies various clinical results that were measured for the particular subject during the clinical trial.

5. The computer-implemented method of claim 1, wherein the one or more sections of the adverse-event report includes an electronic link, wherein the electronic link identifies a corresponding clinical-data item from the first portion of the user interface.

6. The computer-implemented method of claim 1, wherein the one or more sections of the adverse-event report includes one or more empty data fields.

7. The computer-implemented method of claim 1, wherein generating the adverse-event report includes using the machine-learning model to supplement the one or more sections of the adverse-event report with regulatory data.

8. The computer-implemented method of claim 1, further comprising:

receiving modifications to the one or more sections of the adverse-event report;

generating feedback data based on the modifications; and further training the machine-learning model based on the feedback data.

9. A system comprising:

one or more processors; and memory storing thereon instructions that, as a result of being executed by the one or more processors, cause the system to perform operations comprising:

receiving a selection of a particular subject from a plurality of subjects participating on a clinical trial, wherein a plurality of identifiers associated with the plurality of subjects are displayed on a first portion of a user interface associated with a document-processing application, and wherein selecting the particular subject includes selecting an identifier corresponding to the particular subject;

accessing clinical data associated with a particular subject, wherein the clinical data includes a plurality of clinical-data items, wherein each of the plurality of clinical-data items is accessed from one or more clinical-data sources;

causing the plurality of clinical-data items to be displayed on the first portion of the user interface;

receiving a request to generate an adverse-event report, wherein the adverse-event report includes a chronological description of one or more adverse events associated with the particular subject, and wherein the one or more adverse events were identified during participation of the particular subject for the clinical trial;

processing the clinical data using a machine-learning model to generate one or more sections associated with the adverse-event report, wherein the machine-learning model was trained using a training dataset that includes previous adverse-event reports associated with other clinical trials; and causing the one or more sections associated with the adverse-event report to be displayed on a second portion of the user interface of the document-processing application.

10. The system of claim 9, wherein the one or more clinical-data sources include an adverse-event data source that identifies the one or more adverse events, and wherein one or more clinical-data items associated with the adverse-event data source identify demographic data associated with the particular subject.

11. The system of claim 9, wherein the one or more clinical-data sources include concomitant-medications data source that identifies one or more types of medications consumed by the particular subject before or during the clinical trial.

12. The system of claim 9, wherein the one or more clinical-data sources include a laboratory-results data source that identifies various clinical results that were measured for the particular subject during the clinical trial.

13. The system of claim 9, wherein the one or more sections of the adverse-event report includes an electronic link, wherein the electronic link identifies a corresponding clinical-data item from the first portion of the user interface.

14. The system of claim 9, wherein the one or more sections of the adverse-event report includes one or more empty data fields.

15. The system of claim 9, wherein generating the adverse-event report includes using the machine-learning model to supplement the one or more sections of the adverse-event report with regulatory data.

16. The system of claim 9, wherein the instructions further cause the system to perform operations comprising:

receiving modifications to the one or more sections of the adverse-event report;

generating feedback data based on the modifications; and further training the machine-learning model based on the feedback data.

17. A non-transitory, computer-readable storage medium storing thereon executable instructions that, as a result of being executed by one or more processors of a computer system, cause the computer system to perform operations comprising:

receiving a selection of a particular subject from a plurality of subjects participating on a clinical trial, wherein a plurality of identifiers associated with the plurality of subjects are displayed on a first portion of a user interface associated with a document-processing application, and wherein selecting the particular subject includes selecting an identifier corresponding to the particular subject;

accessing clinical data associated with a particular subject, wherein the clinical data includes a plurality of clinical-data items, wherein each of the plurality of clinical-data items is accessed from one or more clinical-data sources;

causing the plurality of clinical-data items to be displayed on the first portion of the user interface;

receiving a request to generate an adverse-event report, wherein the adverse-event report includes a chronological description of one or more adverse events associated with the particular subject, and wherein the one or more adverse events were identified during participation of the particular subject for the clinical trial;

processing the clinical data using a machine-learning model to generate one or more sections associated with the adverse-event report, wherein the machine-learning model was trained using a training dataset that includes previous adverse-event reports associated with other clinical trials; and causing the one or more sections associated with the adverse-event report to be displayed on a second portion of the user interface of the document-processing application.

18. The non-transitory, computer-readable storage medium of claim 17, wherein the one or more clinical-data sources include an adverse-event data source that identifies the one or more adverse events, and wherein one or more clinical-data items associated with the adverse-event data source identify demographic data associated with the particular subject.

19. The non-transitory, computer-readable storage medium of claim 17, wherein the one or more clinical-data sources include concomitant-medications data source that identifies one or more types of medications consumed by the particular subject before or during the clinical trial.

20. The non-transitory, computer-readable storage medium of claim 17, wherein the one or more clinical-data sources include a laboratory-results data source that identifies various clinical results that were measured for the particular subject during the clinical trial.

21. The non-transitory, computer-readable storage medium of claim 17, wherein the one or more sections of the adverse-event report includes an electronic link, wherein the electronic link identifies a corresponding clinical-data item from the first portion of the user interface.

22. The non-transitory, computer-readable storage medium of claim 17, wherein the one or more sections of the adverse-event report includes one or more empty data fields.

23. The non-transitory, computer-readable storage medium of claim 17, wherein generating the adverse-event report includes using the machine-learning model to supplement the one or more sections of the adverse-event report with regulatory data.

24. The non-transitory, computer-readable storage medium of claim 17, wherein the instructions further cause the computer system to perform operations comprising:

receiving modifications to the one or more sections of the adverse-event report;

generating feedback data based on the modifications; and further training the machine-learning model based on the feedback data.

* * * * *